United States Patent [19]
Denny et al.

[11] Patent Number: 5,968,933
[45] Date of Patent: Oct. 19, 1999

[54] DNA-TARGETED ALKYLATING AGENTS

[75] Inventors: William A. Denny; Jeffrey B. Smaill, both of Auckland, New Zealand

[73] Assignees: Auckland Division Cancer Society of New Zealand Inc., New Zealand; Circadian Pharmaceuticals (Australia) Pty. Ltd., Australia

[21] Appl. No.: 08/793,135

[22] PCT Filed: Aug. 23, 1995

[86] PCT No.: PCT/AU95/00520

§ 371 Date: Feb. 19, 1997

§ 102(e) Date: Feb. 19, 1997

[87] PCT Pub. No.: WO96/06831

PCT Pub. Date: Mar. 7, 1996

[30] Foreign Application Priority Data

Aug. 26, 1994 [AU] Australia ............................ PM 7665
Dec. 21, 1994 [AU] Australia ............................ PN 0242

[51] Int. Cl.$^6$ ..................... C07D 235/14; C07D 403/14; C07D 403/06
[52] U.S. Cl. ..................... 514/228.2; 514/255; 514/326; 514/451; 514/459; 544/106; 544/111; 544/56; 544/59; 544/358; 544/359; 544/366; 544/370; 548/414; 548/419; 548/146; 548/148; 548/301.7; 548/302.7
[58] Field of Search ..................... 544/111, 359, 544/366, 370, 56, 59; 548/414, 419, 146, 148, 302.7; 514/228.2, 326, 255, 451, 459

[56] References Cited

U.S. PATENT DOCUMENTS

| | | | |
|---|---|---|---|
| 4,053,472 | 10/1977 | Rufer et al. ............................ | 544/139 |
| 5,225,431 | 7/1993 | Robertson et al. ..................... | 514/389 |
| 5,317,103 | 5/1994 | Baker et al. ............................ | 544/367 |
| 5,567,711 | 10/1996 | Sheppard et al. ....................... | 514/303 |

FOREIGN PATENT DOCUMENTS

9-/12321 10/1990 WIPO ........................... G01N 33/58
WO 97/05292 2/1997 WIPO .

OTHER PUBLICATIONS

Anderson et al, "Synthesis and Antileukemic Activity of 5–Substituted 2,3–Dihydro–6, 7–bis(hydroxymethyl)–1H–pyrrolizine Diesters" *Journal of Medical Chemistry,* vol. 20, No. 6, pp. 812–818, Jun. 1977.

Anderson et al, "Antileukemic Activity of Derivatives of 1,2–Dimethyl–3,4–bis(hydroxymethyl)–5–phenylpyrrole bis(N–methylcarbamate)" *Journal of Medicinal Chemistry,* vol. 23, No. 8, pp. 977–980, Aug. 1979.

Laduréo et al, "Synthesis and Evaluation of Antileukemic Activity of 5–Thienyl–or 5–(2–Furyl)–2,3–dihydro–6, 7–bis(hydroxymethyl)–1H–pyrrolizine Bis(alkylcarbamates) and Derivatives", *Journal of Medicinal Chemistry,* vol. 32, No. 2, pp. 456–461, Feb. 1989.

Chem. Abstr., 108:112449, Okabe et al., JP 62167726.
Gravatt et al., J. Med. Chem., (1994), 37, pp. 4338–4345.
Chem. Abstr. 119:15172, Lee et al., Med. Chem. Res. (1993), 3(2), pp. 79–86.
Chem. Abstr. 122:75755, Nakano et al., (1994), 31 (21st Symposium on nucleic acids Chemistry, 1994) pp. 75–76.
Chem. Abstr. 122:100801, Kogo et al., Nucleic Acids Symp. Ser. (1994), 31 (21st Symposium on Nucleic Acids Chemistry, 1994), pp. 81–82.

Gravatt, G.L., et al., "DNA–Directed Alkylating Agents. 6. Synthesis and Antitumor Activity of DNA Minor Groove–Targeted Aniline Mustard Analogues of Pibenzimol (Hoechst 33258)" *Journal of Medicinal Chemistry,* vol. 37, No. 25, Dec. 9, 1994, no page No.

Lee, M., et al, "DNA Sequence Selective Alkylation and Cytotoxicity of Monoheterocyclic Analogs of Hoechst 33258", *Medicinal Chemistry Research,* vol. 3, 1993 page No. ?.

*Primary Examiner*—Jose' G. Dees
*Assistant Examiner*—Sabiha N. Qazi
*Attorney, Agent, or Firm*—Larson & Taylor

[57] ABSTRACT

The invention relates to novel bis-benzimidazole compounds which have the ability to bind to the minor groove of DNA and to alkylate DNA, to methods of preparing the compounds, and the use of the compounds in the treatement of neoplastic disease.

10 Claims, 1 Drawing Sheet

DNA-TARGETED ALKYLATING AGENTS

This invention relates to a novel class of DNA-targeted alkylating agents, to methods of preparing the novel compounds, and to the use of these compounds in the treatment of neoplastic disease. In particular, the invention relates to novel bisbenzimidazole compounds which in addition to having the ability to bind to the minor groove of deoxyribonucleic acid (DNA) have the ability to alkylate DNA.

BACKGROUND OF THE INVENTION

Alkylating agents are an important class of anticancer drugs, which express their cytotoxic and antitumour effects by forming adducts with cellular DNA. The bisbenzimidazole moiety itself has been reported in the literature as an efficient DNA minor groove binding agent, and a number of compounds of this general structure have been reported to have DNA binding and cytotoxic properties. In particular, the compound pibenzimol (Hoechst 33258), which binds to regions of the minor groove rich in adenine and thymine bases, and its analogues, have been intensively investigated. See for example:

Loewe, V. H. and Urbanietz, I. "Basisch substituierte 2,6-Bis-benzimidazolederivate, eine neue chemotherapeutisch aktive Korperklass" Arz.-Forschung, 1974 24 1927–1933.

Bathini, Y. and Lown, J. W. "Convenient routes to substituted benzimidazoles and imdazolo[4,5-b]pyridines using nitrobenzene as oxidant" Synth. Comm., 1990 20 955–963.

Beerman, T. A., McHugh, M. M., Sigmund, R., Lown, J. W., Rao, K. E. and Bathini, Y. "Effects of analogs of the DNA minor groove binder Hoechst 33258 on topoisomerase II and I mediated activities" Biochim. Biophys. Acta., 1992 1131 53–61.

Kelly, D. P., Bateman, S. A., Martin, R. F., Reum, M. E., Rose, M. and Whittaker, A. R. D. "DNA binding compounds. V. Synthesis and characterisation of boron-containing bisbenzimidazoles related to the DNA minor groove binder Hoechst 33258" Aus. J. Chem., 1994 47 247–262.

Wang, H., Gupta, R. and Lown, J. W. "Synthesis, DNA binding, sequence preference and biological evaluation of minor groove selective N1-alkoxyalkyl bisbenzimidazoles" Anti-Cancer Drug Design, 1994 9 153–180.

A recent publication [Lee, M., Walker, C. D., Eckert, J. M., Bowers, S. K., Montague, D., McAdams, S. and Hartley, J. A., "DNA sequence selective alkylation and cytotoxicity of monoheterocyclic analogues of Hoechst 33258", Med. Chem. Res., 1993 3 79–86] describes three monobenzimidazole mustard compounds. Subsequent to the priority date of this application, a further publication [Gupta, R., Wang, H., Huang, L. And Lown, J. W. "Design, synthesis, DNA sequence preferential alkylation and biological evaluation of N-mustard derivatives of Hoechst 33258 analogues", Anti-Cancer Drug Design, 1995 10 25–41] has described four mixed benzimidazole/benzoxazole mustard analogues of Hoechst 33258.

We have now developed a novel class of bisbenzimidazole compounds which have not only the ability to bind to DNA in the minor groove, but also to alkylate DNA. These compounds show good anti-tumour activity both in vitro and in vivo.

SUMMARY OF THE INVENTION

According to a first aspect, the invention provides compounds of General Formula I

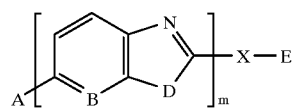

wherein A represents CN, NHR or any one of the formulae IIa–IId;

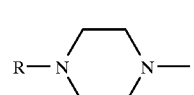

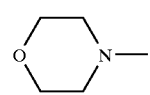

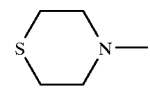

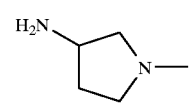

B represents CH or N;
D represents NH, NR, O or S;
X represents $(CH_2)_n(CH_2)_nO$, $(CH_2)_nS$, NHCO, NHCO$(CH_2)_n$, CONH, or CONH$(CH_2)_n$;
E represents any one of the formulae IIIa–IIIc;

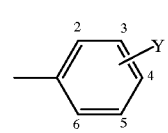

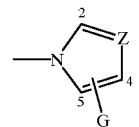

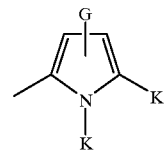

m is 1 or 2,
n is from 0 to 6, and
R is a lower alkyl group optionally substituted with amine and/or hydroxyl functions,
N-oxides thereof, or pharmaceutically acceptable addition salts thereof;
with the proviso that when A is IIa (where R=Me), B is CH, D is NH, X is $(CH_2)_n$, n is 0, m is 1 and E is IIIa, then Y in IIIa is not 4-N$(CH_2CH_2Cl)_2$, 2-OMe, 3-OMe, 4-OMe, 3-Me, 4-Me, 2-Cl, 3-Cl, 4-Cl, 2-$NO_2$, 3-$NO_2$, 4-$NO_2$ or 4-$NMe_2$.

In formula IIa, R is a lower alkyl group optionally substituted with amine and/or hydroxyl functions.

In formula IIIa, Y is one of $N(CH_2CH_2Q)_2$, $N(Me)CH_2CH_2Q$ or $N(Et)CH_2CH_2Q$, together with up to one of $NO_2$, Cl, Br, F, OMe, Me or $CONH_2$ at positions 2 to 6, and Q is Cl, Br, I, OH or $OSO_2Me$.

In formula IIIb, G is up to two of COOR, $CH_2OCONHR$, $CH_2Q$, where R is a lower alkyl group optionally substituted with amine and/or hydroxyl functions, and Q is Cl, Br, I, OH or $OSO_2Me$, and Z is =N— or —CH=.

In formula IIIc, G is up to two of COOR, $CH_2OCONHR$, or $CH_2Q$, where R is a lower alkyl group optionally substituted with amine and/or hydroxyl functions, and Q is Cl, Br, I, OH or $OSO_2Me$, and the K groups are separately H, Me, or together form a carbocyclic ring —$(CH_2)_3$—. Examples of this type of structure have been reported [Anderson, W. K. and Corey, P. F., "Synthesis and antileukemic activity of 5-substituted 2,3-dihydro-6,7-bis(hydroxymethyl)-1H-pyrrolizine diesters", J. Med. Chem., 1977 20 812–818.; Anderson, W. K. and Hala, M. J., "Antileukemic activity of derivatives of 1,2-dimethyl-3,4-bis(hydroxymethyl)-5-phenylpyrrole bis(N-methylcarbamate)", J. Med. Chem., 1979 23 977–980].

For the purposes of this specification, the term "lower alkyl" is to be understood to mean an alkyl group having 1 to 4 carbon atoms.

While only some of the ring structures and substituents within the scope of General Formula I are exemplified herein, both the types of ring structure and the types of substituents are known in the art, and the person skilled in the art will readily be able to synthesise compounds within the scope of the invention other than those specifically described herein. Similarly, such a person will readily be able to synthesize compounds of the invention in which n is 0 to 6.

The compounds of General Formula I form pharmaceutically-acceptable addition salts with both organic and inorganic acids, and these addition salts also form part of the present invention. Examples of suitable acids for salt formation are hydrochloric, sulphuric, phosphoric, acetic, citric, oxalic, malonic, salicylic, malic, fumaric, succinic, ascorbic, maleic, methanesulfonic, isethionic and the like. Certain members of the class of compounds of formula I, containing tertiary alkyl amines, also form N-oxides of these amines, and these N-oxides also form part of the present invention.

The compounds of General Formula I have cytotoxic and anticancer activity, and are useful as antitumour agents.

Therefore according to a second aspect, the invention provides a pharmaceutical composition comprising a compound of General Formula I, together with a pharmaceutically acceptable carrier.

According to a third aspect, the invention provides a method of treatment of neoplastic disease, comprising the step of administering an effective dose of a compound of General Formula I to a mammal in need of such treatment.

Preferably the dose administered will be in the range of 1 to 200 mg/kg/body weight. This may be administered as a single dose, or in divided doses. The compound of General Formula I may be administered by any suitable route, for example by intravenous, intramuscular, subcutaneous or intra-tumour injection, or may be administered orally or topically.

It will be appreciated that the amount of a compound of the invention required for use in treatment will vary not only with the particular compounds selected but also with the route of administration, the nature of the condition being treated, and the age and condition of the individual being treated, and will ultimately be at the discretion of the attendant physician or veterinarian.

According to a fourth aspect, the invention provides methods of synthesis of compounds of the invention, in accordance with the reaction schemes set out herein. It will be appreciated that the most suitable reaction scheme for synthesis of a given compound of the invention will depend upon the nature of the individual compound. A skilled person will be able to select the most suitable scheme for the desired purpose.

Thus the invention provides a method of synthesis of a compound of General Formula I, said method comprising steps selected from the group consisting of a) converting a nitrile to a corresponding imine ether hydrochloride, and reacting said imine ether hydrochloride with a freshly prepared phenylene diamine;

b) treating an acid with borane-dimethyl sulphide to yield an alcohol; converting the alcohol to an aldehyde by oxidation under Swern conditions; reacting the aldehyde with a phenylenediamine to give a monobenzimidazole compound of formula I; converting the monobenzimidazole compound to a corresponding imine ether and coupling with a diaminobenzene derivative by cupric ion-promoted oxidation to yield a bisbenzimidazole compound of formula I;

c) converting a monomustard acid to an aldehyde, coupling the aldehyde with a phenylenediamine to yield a monobenzimidazole compound of formula I together with the corresponding alcohol; converting the monobenzimidazole to the corresponding imine ether, coupling the imine ether with a diaminobenzene derivative and optionally halogenating to yield a monomustard bisbenzimidazole compound of formula I;

d) coupling a carboxylic acid derivative of an aniline mustard or aniline half-mustard with a freshly-prepared benzimidazole phenylenediamine using PPE, to yield a mustard or half-mustard bisbenzimidazole of formula I;

e) converting an imidazole dicarboxylic acid to the corresponding diethyl ester, subjecting said ester to N-alkylation with an alkyl bromide to yield a t-butyl ester derivative, selectively hydrolysing the t-butyl ester derivative to yield a carboxylic acid, converting the carboxylic acid to the acid chloride, coupling said acid chloride to a nitroaniline to yield an amide, subjecting said amide to reduction and acid-catalysed ring closure to yield a benzimidazole, coverting said benzimidazole to the corresponding diol by hydride reduction, and bis-carbamate protecting said diol; and f) directly coupling a carboxylic acid and a freshly prepared phenylenediamine using PPE to yield a bisbenzimidazole, subjecting said benzimidazole to hydride reduction to yield a diol and biscarbamate protecting said diol.

DETAILED DESCRIPTION OF THE INVENTION

Figure 1:
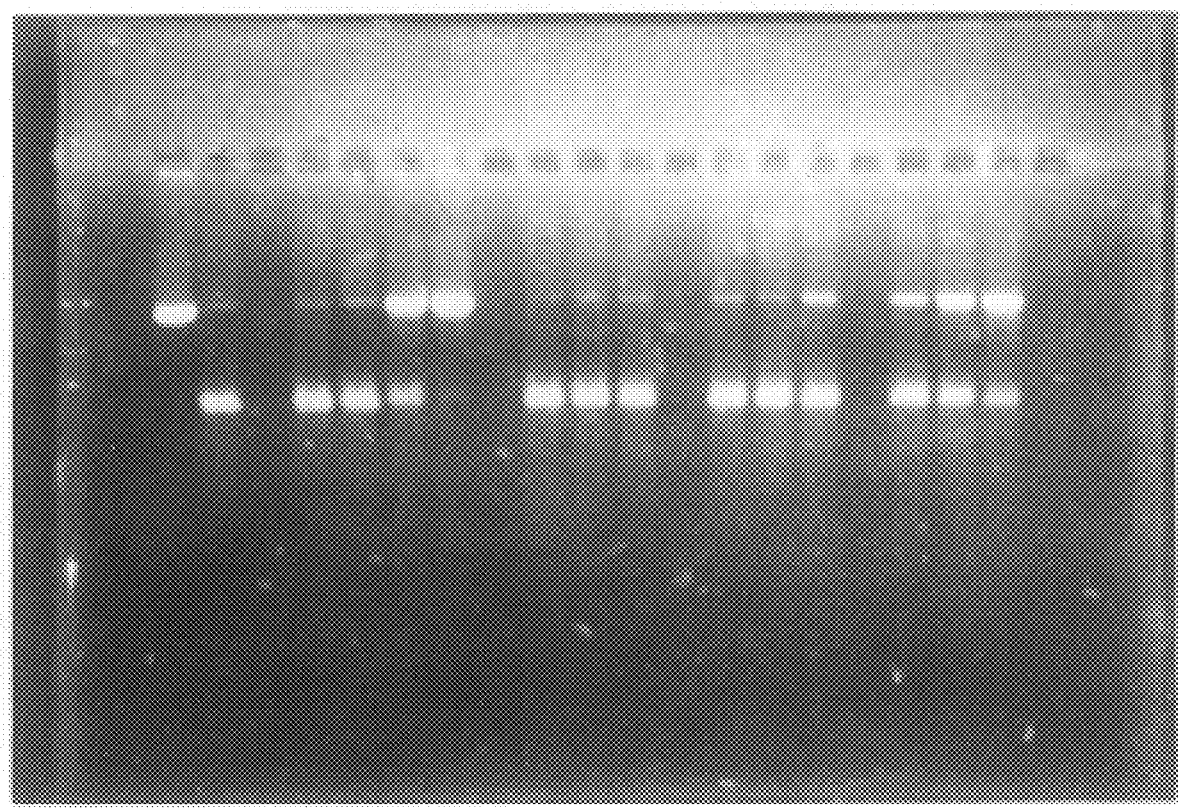

The invention will now be described in detail by way of reference only to the following non-limiting examples, and to FIG. 1, which shows the results of agarose gel electrophoresis of pSV2gpt DNA treated with representative compounds of the invention or with known alkylating agents. The lanes are as follows, reading from left to right: (1) Untreated DNA, no drug; (2) Denatured DNA, no drug; (3)

blank; (4–5) Denatured DNA in the presence of chloroambucil half mustard; 20, 50 μM respectively; (6–7) Denatured DNA in the presence of chlorambucil; 20, 50 μM respectively; (8) blank; (9–11) Denatured DNA in the presence of compound 3; 0.5, 1, 2 μM respectively; (12) blank; (13–15) Denatured DNA in the presence of compound 5; 0.5, 1, 2 μM respectively; (16) blank; (17–19) Denatured DNA in the presence of compound 6; 0.5, 1, 2 μM respectively.

Abbreviations used herein are as follows:

| | |
|---|---|
| HRMS | High Resolution Mass Spectrometry |
| PPE | polyphosphate ester |
| Ms | methanesulphonyl |
| DMF | dimethylformamide |
| THF | tetrahydrofuran |

The compounds of formula I and the acid addition salts and N-oxides thereof may be prepared by the processes outlined in Schemes 1–6.

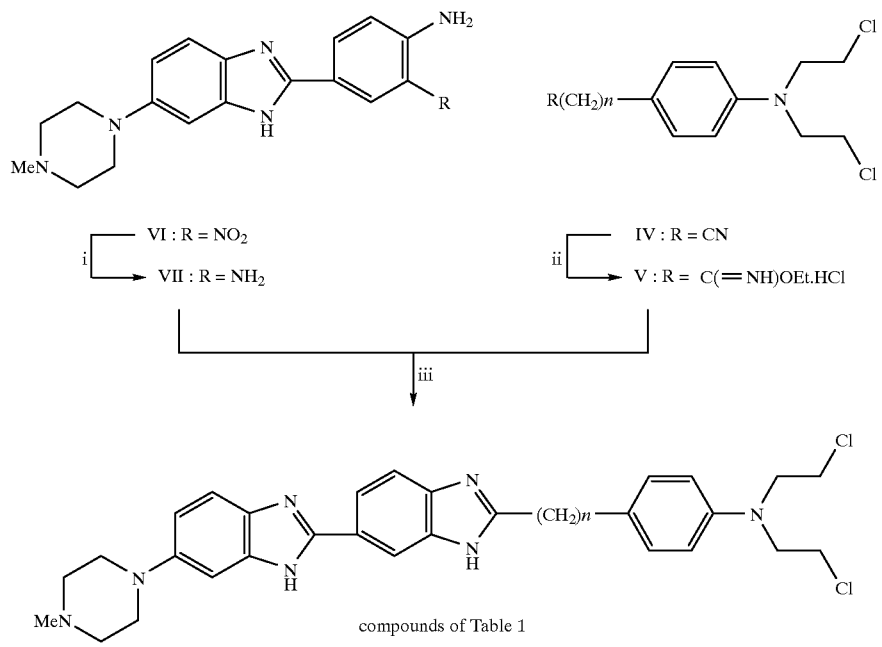

Scheme 1

| | |
|---|---|
| i | $H_2$/Rh — $Al_2O_3$/Pt — C/EtOH/glacial AcOH. |
| ii | EtOH/HCl$_{(g)}$/(0° C. to 20° C.)/2 days. |
| iii | EtOH/glacial AcOH/3 h. |

In Scheme 1, conversion of nitriles (IV) to the corresponding imine ether hydrochlorides (V), followed by reaction of these with freshly prepared phenylenediamine (VII), gave moderate yields (ca. 20%) of the desired compounds of formula I (compounds 1 to 4 of Table 1).

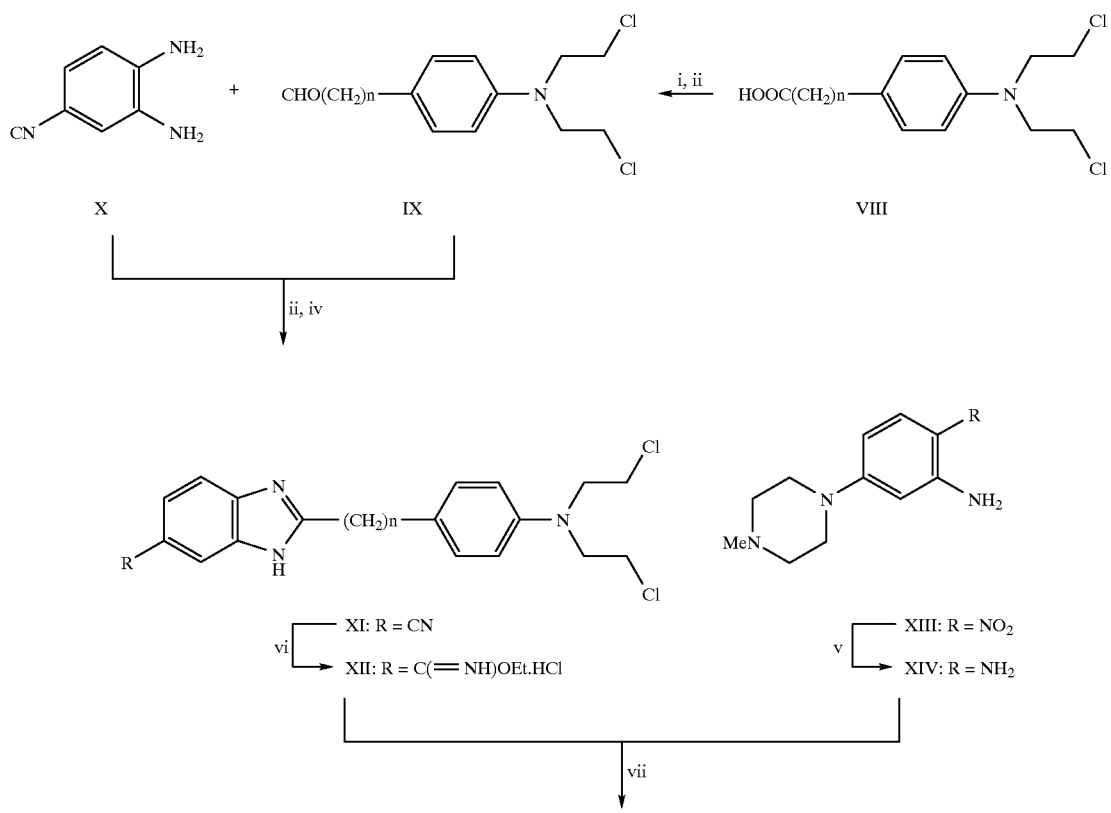

Scheme 2

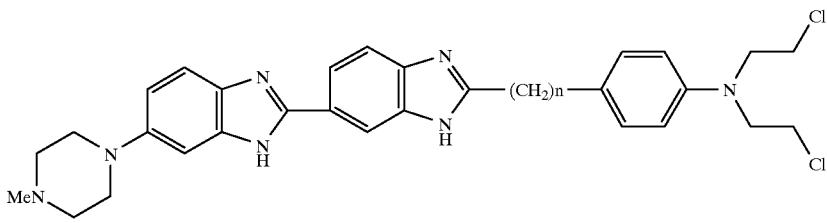

compounds of Table 1

Scheme 2

| | |
|---|---|
| i | $BH_3.DMS/THF/0°$ C. |
| ii | $DMSO/(COCl)_2/THF/-78°$ C.; $Et_3N/-78°$ C. to 20° C. |
| iii | $Cu(OAc)_2/MeOH_{(aq)}/$__/20 min. |
| iv | $Na_2S_{(aq)}$. |
| v | $Pt-C/Rh-Al_2O_3/60$ psi $H_2/AcOH$. |
| vi | $HCl_{(g)}/EtOH/0°$ C. to 20° C./2 days. |
| vii | AcOH/100° C./2 h. |

Scheme 2 outlines an alternative method of synthesis of benzimidazole derivatives representative of formula I. Treatment of acids (VIII) with borane-dimethyl sulphide gave the corresponding crude alcohols, which were in turn oxidised under Swern conditions to the aldehydes (IX). Reaction of these aldehydes with the phenylenediamine (X) gave the desired monobenzimidazole compounds of formula I (compounds 7 to 10 of Table I). Conversion of these compounds to the corresponding imine ethers, followed by $Cu^{2+}$-promoted oxidative coupling of these with the diaminobenzene derivative (XIV) gave good yields of the desired bisbenzimidazole compounds of formula I (compounds 2, 4 to 6 of Table 1).

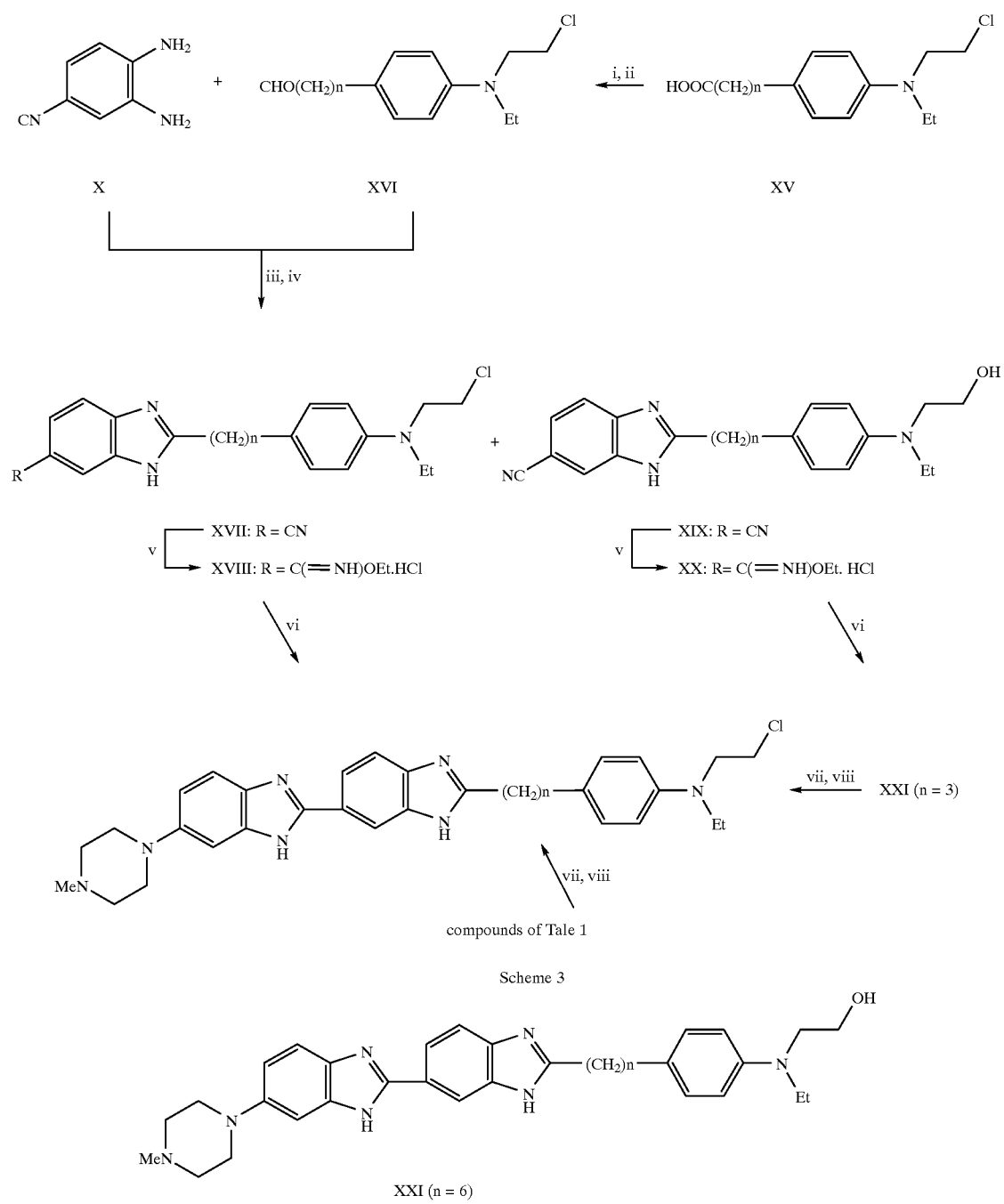

Scheme 3

| | |
|---|---|
| i | BH$_3$.DMS/THF/0° C. |
| ii | DMSO/(COCl)$_2$/THF/−78° C.; Et$_3$N/−78° C. to 20° C. |
| iii | Cu(OAc)$_2$ (n = 3); CuCl$_2$ (n = 2,6)/MeOH$_{(aq)}$/Δ/20 min. |
| iv | Na$_2$S$_{(aq)}$. |
| v | HCl$_{(g)}$/EtOH/0° C. to 20° C./2 days. |
| vi | AcOH/100° C./3–8 h. |
| vii | MsCl/pyridine/CH$_2$Cl$_2$/0° C. |
| viii | LiCl/DMF/140° C. |

In Scheme 3, the monomustard acids (XV) were similarly converted to the aldehydes (XVI), which were similarly coupled to (X) to give monobenzimidazole compounds of formula I (compounds 11 to 13 of Table 1), together with the corresponding alcohols (XIX). The use of CuCl$_2$ as a coupling catalyst minimised hydrolysis to the alcohols.

Further coupling of the imine ethers of the monobenzimidazoles with the diaminobenzene derivative (XIV), followed by halogenation with MsCl.LiCl where necessary, gave the desired monomustard bisbenzimidazole compounds of formula I (compounds 14 to 16 of Table 1).

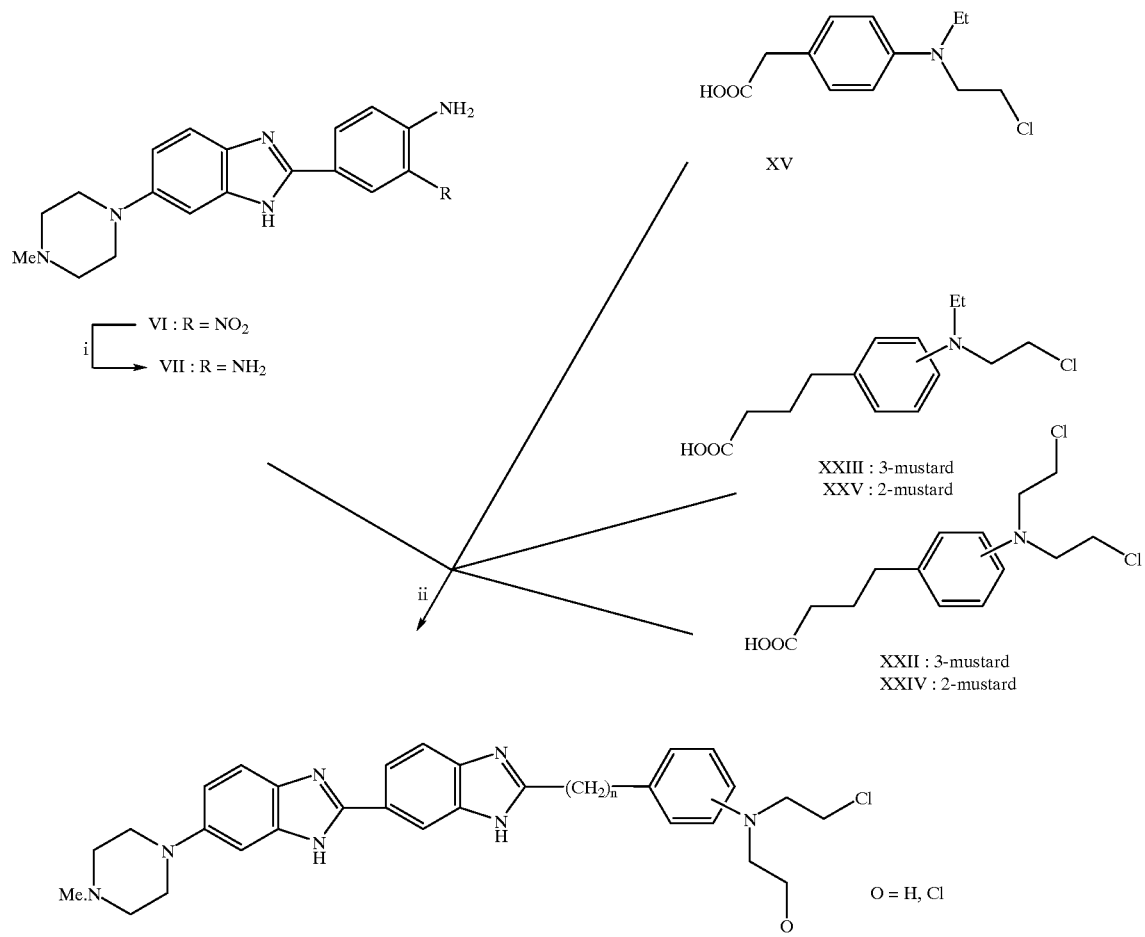

Scheme 4

| i | Pt—C/Rh—Al₂O₃/60 psi H₂/EtOAc/MeOH |
| ii | PPE (polyphosphate ester)/100° C./2 h |

Scheme 4 outlines the preferred method of synthesis of bisbenzimidazole mustard and bisbenzimidazole half mustard derivatives representative of formula I. coupling of the respective acids (XV), (XXII–XXV) with freshly prepared phenylenediamine (VII) using PPE gave the desired half mustard and mustard bisbenzimidazole compounds of formula I (compounds 17 to 21 of Table 1).

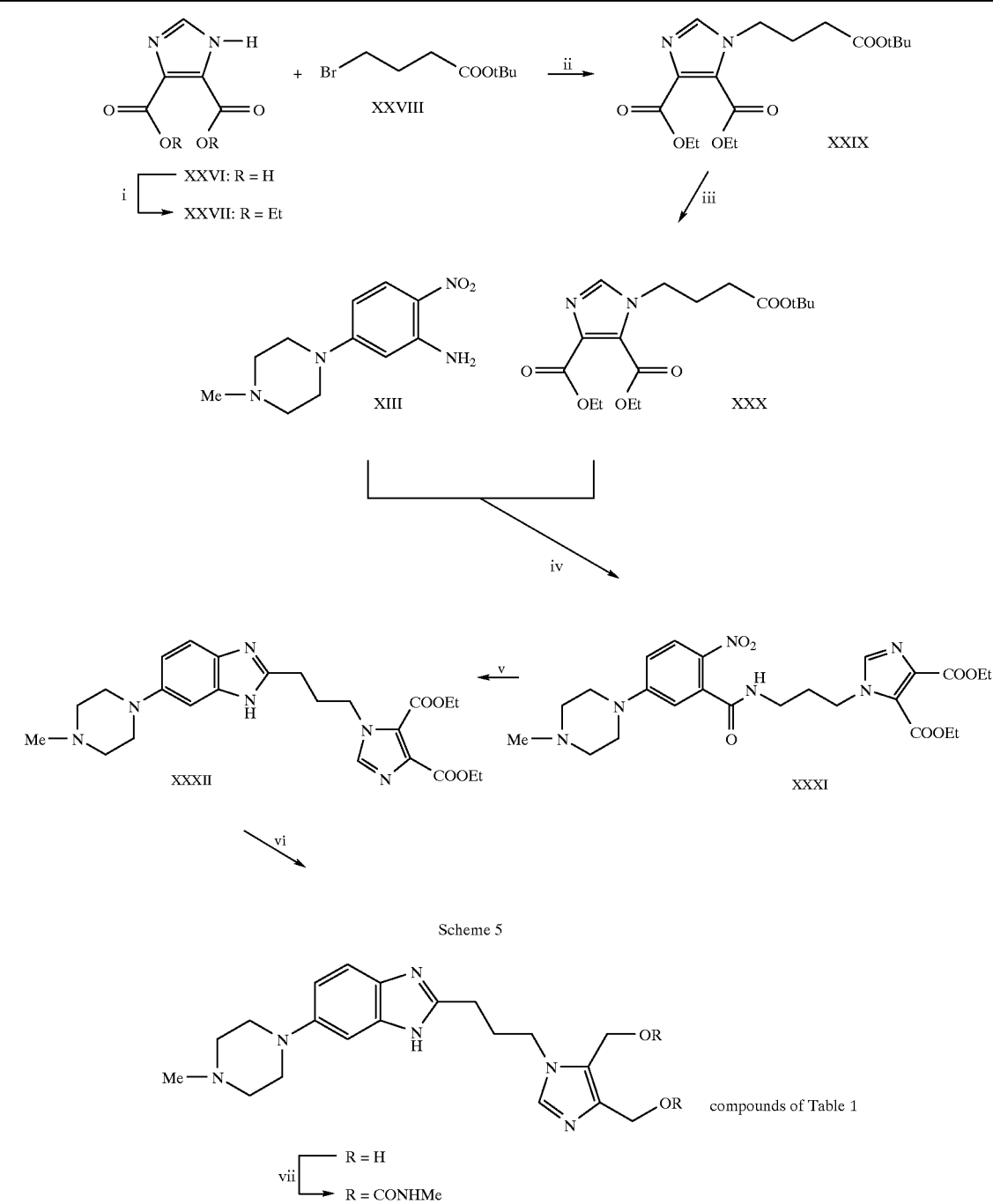
Scheme 5
| | |
|---|---|
| i | EtOH/SOCl$_2$/reflux. |
| ii | K$_2$CO$_3$/DMF/Δ. |
| iii | HCOOH/25° C. to 50° C./20 h. |
| iv | SOCl$_2$/DMF; XIII/THF/2 h. |
| v | Pt-C/Rh-Al$_2$O$_3$/60 psi H$_2$/EtOH; HCl(g)/0° C. to 70° C./24 h. |
| vi | LiAlH$_4$/THF/0° C./2 h. |
| vii | MeNCO/Bu$_2$Sn(OAc)$_2$/CH$_2$Cl$_2$. |

In Scheme 5, the imidazole dicarboxylic acid (XXVI) is converted to its diethyl ester (XXVII) which is then N-alkylated with the alkyl bromide (XXVIII). Selective hydrolysis of the resulting t-butyl ester derivative (XXIX) gave the carboxylic acid (XXX), which was then converted to the acid chloride and coupled to the nitroaniline (XIII) to give the amide (XXXI). Reduction and acid catalysed ring closure of amide (XXXI) gave the benzimidazole (XXXII) disclosures of which are incorporated herein by this reference. While Scheme 4 as previously described was successful in enabling production of the diol derivative of General Formula I, 2-[2-[N-(4,5-bishydroxymethyl)imidazolyl]ethyl]-5-(1-methyl-4-piperazinyl)benzimidazole, the yield was very low. Scheme 5 as presently described can be used to make the diol derivative.

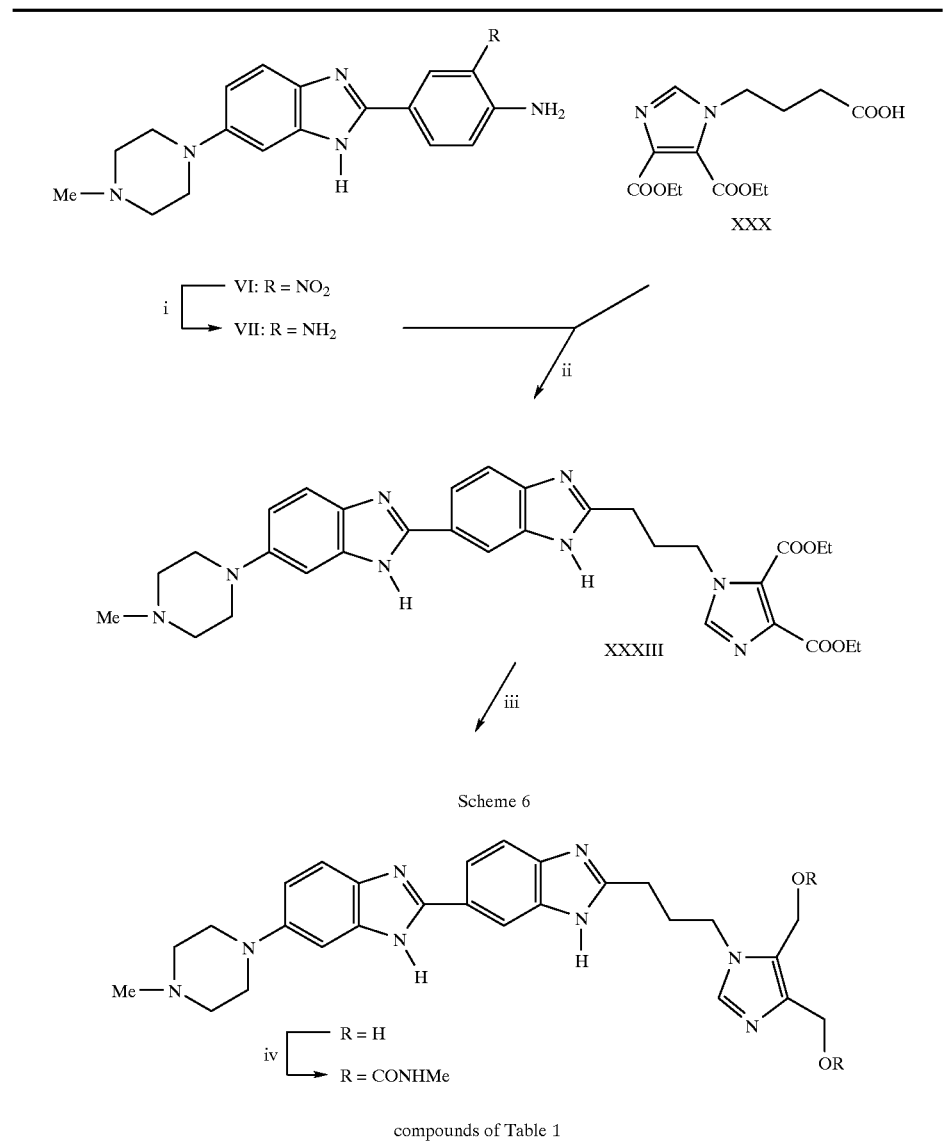

Scheme 6

| | |
|---|---|
| i | Pt-C/Rh-Al$_2$O$_3$/60 psi H$_2$/EtOAc/MeOH. |
| ii | PPE (polyphosphate ester)/100° C./2 h. |
| iii | LiAlH$_4$/THF/0° C./2 h. |
| iv | MeNCO/Bu$_2$Sn(OAc)$_2$/CH$_2$Cl$_2$. | which upon hydride reduction, and biscarbamate protection of the resulting diol, gave the desired benzimidazole compounds of formula I (compounds 22 and 23 of Table 1). Scheme 5 is a modification of Scheme 4 as described in the priority documents in respect of this application, Australian Patent Applications No. PM 7665 and PN 0242, the entire In Scheme 6, direct coupling of the carboxylic acid (XXX) and freshly prepared phenylenediamine (VII) using PPE gave the bisbenzimidazole (XXXIII) which upon hydride reduction, and biscarbamate protection of the resulting diol, gave the desired bisbenzimidazole compounds of formula I (compounds 24 and 25 of Table 1).

Table 1 gives physicochemical data for 25 compounds within the General Formula I, representative of it, and which have been prepared by the processes of the invention.

TABLE 1

Structures and physicochemical properties of representative compounds of formula I
Diagrams for Table 1

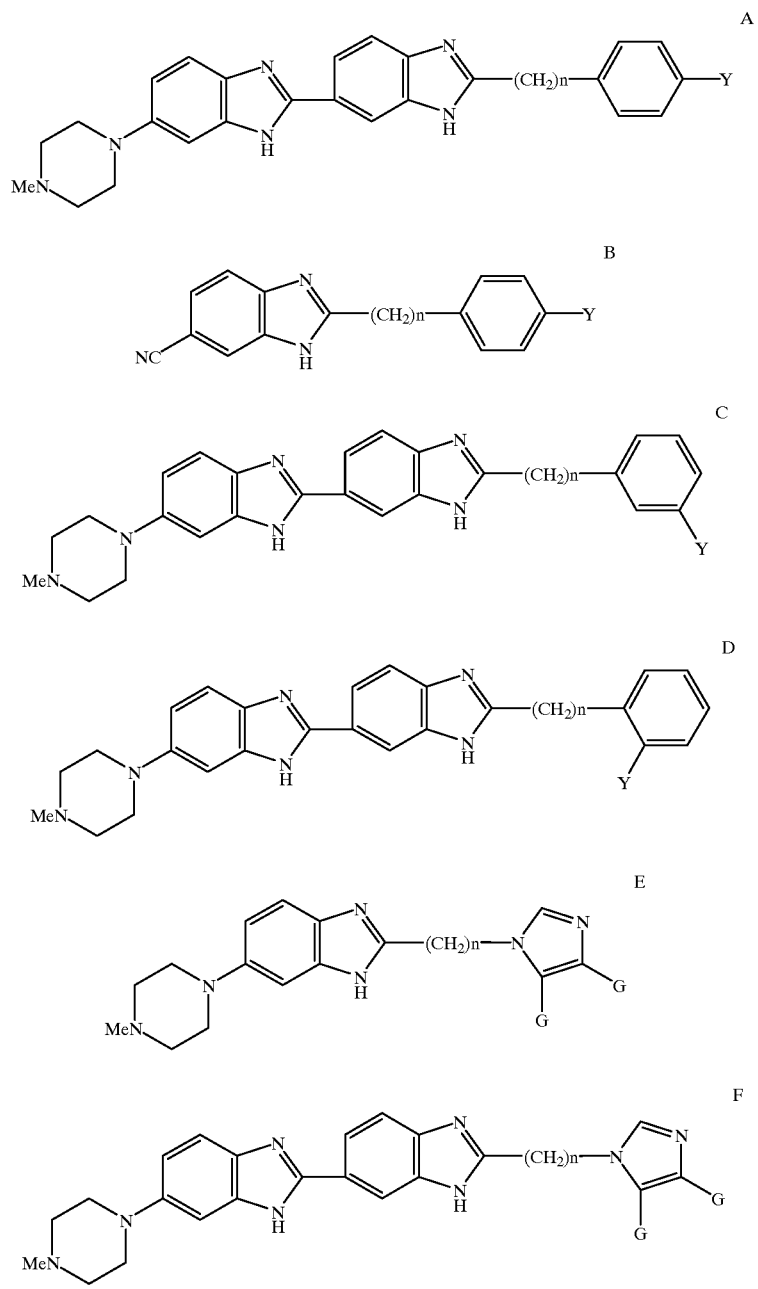

| No | form | n | Y | mp(° C.) | formula | analyses |
|----|------|---|---|----------|---------|----------|
| 1 | A | 0 | N(Me)CH$_2$CH$_2$Cl | >300 | C$_{28}$H$_{30}$NCl.3HCl.3H$_2$O | C,H,N |
| 2 | A | 0 | N(CH$_2$CH$_2$Cl)$_2$ | >300 | C$_{29}$H$_{31}$N$_7$Cl$_2$.3HCl.1.5H$_2$O | C,H,N,Cl |
| 3 | A | 1 | N(CH$_2$CH$_2$Cl)$_2$ | >300 | C$_{30}$H$_{33}$N$_7$Cl$_2$.3HCl | C,H,N |
| 4 | A | 2 | N(CH$_2$CH$_2$Cl)$_2$ | >300 | C$_{31}$H$_{35}$N$_7$Cl$_2$.3HCl.2H$_2$O | C,H,N |
| 5 | A | 3 | N(CH$_2$CH$_2$Cl)$_2$ | >300 | C$_{32}$H$_{37}$N$_7$Cl$_2$.3HCl.H$_2$O | C,H,N |
| 6 | A | 6 | N(CH$_2$CH$_2$Cl)$_2$ | >300 | C$_{35}$H$_{43}$N$_7$Cl$_2$.3HCl.4H$_2$O | C,H,N |
| 7 | B | 0 | N(CH$_2$CH$_2$Cl)$_2$ | 80 | C$_{18}$H$_{16}$Cl$_2$N$_4$ | C,H,N,Cl |

TABLE 1-continued

| | | | | | | |
|---|---|---|---|---|---|---|
| 8 | B | 2 | N(CH$_2$CH$_2$Cl)$_2$ | 50 | C$_{20}$H$_{20}$Cl$_2$N$_4$ | C,H,N |
| 9 | B | 3 | N(CH$_2$CH$_2$Cl)$_2$ | gum | C$_{21}$H$_{22}$Cl$_2$N$_4$.H$_2$O | C,H,N |
| 10 | B | 6 | N(CH$_2$CH$_2$Cl)$_2$ | gum | C$_{24}$H$_{28}$N$_4$Cl$_2$ | HRMS |
| 11 | B | 3 | N(Et)CH$_2$CH$_2$Cl | gum | C$_{21}$H$_{23}$ClN$_4$ | HRMS |
| 12 | B | 2 | N(Et) CH$_2$CH$_2$Cl | gum | C$_{20}$H$_{21}$ClN$_4$ | HRMS |
| 13 | B | 6 | N(Et)CH$_2$CH$_2$Cl | gum | C$_{24}$H$_{29}$ClN$_4$ | HRMS |
| 14 | A | 3 | N(CH$_2$CH$_2$Cl)$_2$ | >300 | C$_{32}$H$_{38}$ClN$_7$.4HCl.4H$_2$O | C,H,N |
| 15 | A | 2 | N(Et)CH$_2$CH$_2$CL | >300 | C$_{31}$H$_{36}$ClN$_7$.4HCl.H$_2$O | C,H,N,Cl |
| 16 | A | 6 | N(Et)CH$_2$CH$_2$Cl | >300 | C$_{35}$H$_{44}$ClN$_7$.4HCl.10H$_2$O | C,H,N,Cl |
| 17 | A | 1 | N(Et)CH$_2$CH$_2$Cl | >300 | C$_{30}$H$_{37}$ClN$_7$.3HCl.3H$_2$O | C,H,N |
| 18 | C | 3 | N(CH$_2$CH$_2$Cl)$_2$ | 220(d) | C$_{32}$H$_{37}$Cl$_3$N$_7$.1.5H$_2$O | C,H,N,Cl |
| 19 | C | 3 | N(Et)CH$_2$CH$_2$Cl | 220(d) | C$_{32}$H$_{38}$ClN$_7$ | C,H,N,Cl |
| 20 | D | 3 | N(CH$_2$CH$_2$Cl)$_2$ | 230(d) | C$_{32}$H$_{37}$Cl$_2$N$_7$ | C,H,N,Cl |
| 21 | D | 3 | N(Et)CH$_2$CH$_2$Cl | 220(d) | C$_{32}$H$_{38}$ClN$_7$ | C,H,N,Cl |
| 22 | E | 3 | CH$_2$OH | 197–200 | C$_{20}$H$_{28}$N$_6$O$_2$.H$_2$O | C,H,N |
| 23 | E | 3 | CH$_2$OCONHCH$_3$ | 168–169 | C$_{24}$H$_{34}$N$_8$O$_4$ | C,H,N |
| 24 | F | 3 | CH$_2$OH | 238–240 | C$_{27}$H$_{32}$N$_8$O$_2$ | C,H,N |
| 25 | F | 3 | CH$_2$OCONHCH$_3$ | 176–177 | C$_{31}$H$_{38}$N$_{10}$O$_4$ | HRMS |

*HRMS: High resolution mass spectroscopy

The following Examples illustrate the preparation of compounds representative of the general formula I.

Elemental analyses were carried out in the Microchemical Laboratory, University of Otago. Melting points were determined on an Electrothermal apparatus using the supplied, stem-corrected thermometer, and are as read. NMR spectra were obtained on either Bruker AM-400 or CW-60 spectrometers (Me$_4$Si). Some $^{13}$C resonances, particularly quaternary carbons of benzimidazole ring systems, proved difficult to observe and remain unassigned. Mass spectra were obtained on an AEI MS-30 spectrometer at nominal 5000 resolution. Fluorescence spectra were obtained on a Hitachi F-2000 spectrofluorimeter.

The names of the compounds referred to herein which were disclosed in the priority documents in respect of this specification, Australian Provisional Patent Applications No. PM 7665 and No. PN 0242, have been revised in order to accord with IUPAC recommendations. However, these compounds are the same as those which were disclosed in the priority documents.

EXAMPLE 1

Preparation of 2-[2-[4-(N, N-bis(2-chloroethyl) aminolphenyl]-5-benzimidazolyl]-5-(1-methyl-4-piperazinyl)benzimidazole (compound 2 of Table 1) via the method of Scheme 1

Example of General Procedure

Dry HCl gas was slowly bubbled into a suspension of 4-[N,N-bis(2-chloroethyl)amino]-benzonitrile (IV: n=0) [Degutis, J.; Sukelienne, D. Synthesis and some reactions of nitrites of N,N-bis(2-chloroethyl)aminophenylalkanoic acids. Zh. Obshch. Khim., 1961 31 3326–3330; Chem. Abstr., 1962, 57 3354e] (0.73 g, 3 mmol) in dry EtOH (30 mL) maintained at 0–57° C., and addition of HCl was continued until the solution became saturated. The mixture was brought to room temperature and stirred for a further 48 h, and the resulting suspension was then concentrated under reduced pressure to give the crude imine ether hydrochloride (V, n=0) which was used without purification.

A solution of 2-(3-nitro-4-aminophenyl)-6-(1-methyl-4-piperazinyl)benzimidazole (VI) [Loewe, H.; Urbanietz, J., "Basisch substituerte 2,6-bisbenzimidazol-derivat, eine neue chemotherapeutisch aktive korperclasse", Arzneim-Forsch. (Drug Design), 1974 24 1927–1933] (1.06 g, 3 mmol) in EtOH/glacial AcOH (1:1, 60 mL) was hydrogenated over Rh-Al$_2$O$_3$/Pt-C at 60 psi H$_2$ for 12 h. After this time the catalysts were removed by filtration and the solution of crude diamine (VII) was added immediately to the imine ether hydrochloride (V, n=0) prepared above. The slurry was refluxed under N$_2$ for 3 h and concentrated under reduced pressure, and the crude residue was basified with concentrated ammonia and partitioned between EtOAc and water. The aqueous phase was repeatedly extracted with portions of EtOAc, and the combined organic phases were dried (Na$_2$SO$_4$), filtered and concentrated, and the residue was chromatographed on Al$_2$O$_3$ (grade III). Elution with EtOAc/MeOH (99:1) afforded compound 2 of Table 1 (0.30 g, 17% yield) as a pale yellow foam. Trihydrochloride, mp (MeOH/EtOAc) >300° C. $^1$H NMR (CD$_3$OD) δ 8.52 (d, $J_{4,6}$=1.4 Hz, 1 H, H-4), 8.25 (dd, $J_{6,7}$=8.6 Hz and $J_{4,6}$=1.4 Hz, 1 H, H6), 8.11 (d, $J_{2'',3''}$=9.1 Hz, 2 H, H-2'',H-6''), 8.03; (d, $J_{6,7}$=8.6 Hz, 1 H, H-7), 7.77 (d, $J_{6',7'}$=9.1 Hz, 1 H, H-7'), 7.44 (dd, $J_{6',7'}$=9.1 Hz and $J_{4',6'}$=2.0 Hz, 1 H, H-6'), 7.37 (d, $J_{4',6'}$=2.0 Hz, 1 H, H-4'), 7.10 (d, $J_{2'',3''}$=9.1 Hz, 2 H, H-3'',H-5''), 4.00 (br d, J=11.5 Hz, 2 H, piperazinyl methylene), 3.96 (br t, J=6.5 Hz, 4 H, NCH$_2$CH$_2$Cl), 3.80 (br t, J=6.5 Hz, 4 H, NCH$_2$CH$_2$Cl), 3.70 (br d, J=12.0 Hz, 2 H, piperazinyl methylene), 3.30 (br m, 4 H, piperazinyl methylene), 3.01 (s, 3 H, NCH$_3$). $^{13}$C NMR δ 154.09, 153.42, 151.08, 149.02, 136.20, 134.35, 133.73, 131.44, 127.63, 126.31, 121.36, 119.94, 116.02, 115.72, 114.14, 113.99, 109.92, 100.80, 54.59, 53.85, 48.34, 43.63, 41.46. Fluorescence excitation $v_{max}$ (MeOH) 383 nm, emission $\lambda_{max}$ (MeOH) 510 nm. Anal. (C$_{29}$H$_{31}$N$_7$Cl$_2$.3HCl.1.5H$_2$O) C,H,N,Cl.

Further elution with EtOAc/MeOH (19:1) yielded 2-[2-methyl-5-benzimidazolyl]-6-(1-methyl-4-piperazinyl)-benzimidazole (0.31 g, 27% yield), mp (MeOH/EtOAc) >260° C. (dec.). $^1$H NMR ((CD$_3$)$_2$SO/D$_2$O) δ 8.62 (s, 1 H, H-4), 8.28 (d, $J_{6,7}$=8.4 Hz, 1 H, H-6), 8.03 (d, $J_{6,7}$=8.4 Hz, 1 H, H-7), 7.74 (d, $J_{6',7'}$=9.1 Hz, 1 H, H-7'), 7.38 (dd, $J_{6',7'}$=9.1 Hz and $J_{4',6'}$=1.7 Hz, 1 H, H-6'), 7.28 (d, $J_{4',6'}$=1.7 Hz, 1 H, H-4'), 3.94 (br d, J=11.9 Hz, 2 H, piperazinyl methylene), 3.61 (br d, J=10.8 Hz, 2 H, piperazinyl methylene), 3.27 (t, J=11.9 Hz, 2 H, piperazinyl methylene), 3.20 (t, J=11.4 Hz, 2 H, piperazinyl methylene), 2.91 (s, 3 H, CH$_3$), 2.88 (s, 3 H, CH$_3$). $^{13}$C NMR δ 154.25, 148.61, 146.95, 133.70, 133.04, 131.44, 126.09, 124.45, 119.95, 117.22, 114.69, 114.33, 113.55, 98.64, 51.94, 46.01, 41.76, 12.60. Anal. (C$_{20}$H$_{23}$N$_6$.5H$_2$O) C,H,N.

EXAMPLE 2

Preparation of 2-[2-[4-(N-methyl-N-(2-chloroethyl)amino)phenyl]-5-benzimidazolyl]-5-(1-methyl-4-piperazinyl)benzimidazole (compound 1 of Table 1)

A solution of 4-fluorobenzonitrile (5.35 g, 44.2 mmol) in DMSO (30 mL) containing excess methylaminoethanol was heated with stirring to 120° C. for 8 h. The solution was then cooled and concentrated under reduced pressure. The crude residue was partitioned between $H_2O$/EtOAc and the organic phase then washed with water (×2), dried ($Na_2SO_4$), filtered and concentrated and percolated through a pad of $SiO_2$ ($CH_2Cl_2$ then EtOAc elution) to give 4-(N-methyl,N-(hydroxyethyl)amino)benzonitrile (5.6 g, 72% yield) as a colourless liquid, which was used without further purification. A solution of the above nitrile (5.6 g, 31.8 mmol) and $Et_3N$ (8.8 mL, 63.6 mmol) in dry $CH_2Cl_2$ (50 mL) was treated at 0° C. with MsCl (3.0 mL, 38.2 mmol). The mixture was stirred for 20 min and partitioned between aqueous $NaHCO_3$/EtOAc. The organic phase was then dried ($Na_2SO_4$), filtered and concentrated under reduced pressure to yield the crude mesylate, which was treated with excess LiCl in DMF (25 mL) at 140° C. for 5 min with rapid stirring. Excess DMF was removed under reduced pressure and the residue was partitioned between $H_2O$/EtOAc. Workup of the organic layer and chromatography of the residue on $SiO_2$ and elution with petroleum ether/EtOAc (3:1) afforded pure 4-(N-methyl,N-(2-chloroethyl)amino)benzonitrile (3.6 g, 58% yield), mp (petroleum ether/$CH_2Cl_2$) 104.5–105.5° C. $^1H$ NMR ($CDCl_3$) δ 7.48 (d, $J_{2,3}$=9.1 Hz, 2 H, H-2,H-6), 6.67 (d, $J_{2,3}$=9.1 Hz, 2 H, H-3, H-5), 3.74 (complex t, J=7.3 Hz, 2 H, $NCH_2CH_2Cl$), 3.64 (complex t, J=7.3 Hz, 2 H, $NCH_2CH_2Cl$), 3.09 (s, 3 H, $NCH_3$); $^{13}C$ NMR δ 150.95, 133.66, 120.30, 111.50, 98.50, 53.77, 40.16, 39.02. Anal. ($C_{10}H_{11}ClN_2$) C,H,N.

Reaction of the crude imine ether hydrochloride prepared from the above nitrile with (VII) as above, followed by chromatography on alumina (grade III) (elution with EtOAc then EtOAc/1–3% MeOH) afforded compound 1 of Table 1 (0.57 g, 13% yield). Trihydrochloride salt, mp (MeOH/EtOAc) >300° C. $^1H$ NMR ($CD_3OD/D_2O$) δ 8.16 (d, $J_{4,6}$=1.6 Hz, 1 H, H-4), 8.00 (dd, $J_{6,7}$=8.6 Hz and $J_{4,6}$=1.6 Hz, 1 H, H-6), 7.87 (d, $J_{6,7}$=8.6 Hz, 1 H, H-7), 7.82 (d, $J_{2'',3''}$=9.0 Hz, 2 H, H-2'',H-6''), 7.68 (d, $J_{6',7'}$=8.9 Hz, 1 H, H-7'), 7.32 (dd, $J_{6',7'}$=8.9 Hz and $J_{4',6'}$=2.1 Hz, 1 H, H-6'), 7.29 (d, $J_{4',6'}$=2.1 Hz, 1 H, H-4'), 6.80 (d, $J_{2'',3''}$=9.0 Hz, 2 H, H-3'',H 5''), 3.95 (br d, J=12.1 Hz, 2 H, piperazinyl methylene), 3.72–3.68 (m, 6 H, $NCH_2CH_2Cl$ and piperazinyl methylene), 3.31 (t, J=12.4 Hz, 2 H, piperazinyl methylene), 3.24 (t, J=11.8 Hz, 2 H, piperazinyl methylene), 3.04 (s, 3 H, $NCH_3$), 2.99 (s, 3 H, $NCH_3$). $^{13}C$ NMR δ 154.15, 153.42, 150.44, 148.16, 136.00, 134.03, 133.53, 130.62, 127.41, 125.41, 120.26, 119.31, 115.88, 115.68, 113.17, 112.95, 108.54, 100.50, 54.45, 54.20, 48.06, 43.81, 42.00, 39.30. Fluorescence excitation $\lambda_{max}$ (MeOH) 397 nm, emission $\lambda_{max}$ (MeOH) 511 nm. Anal. ($C_{28}H_{30}NCl.3HCl.3H_2O$) C,H,N.

EXAMPLE 3

Preparation of 2-[2-[[4-(N,N-bis(2-chloroethyl)amino)phenyl]methyl]-5-benzimidazolyl]-5-(1-methyl-4-piperazinyl)benzimidazole (compound 3 of Table 1)

A similar reaction between (VII) and the crude imine ether hydrochloride (V, n=1) (prepared from the nitrile (IV, n=1)) [Degutis, J.; Sukelienne, D., "Synthesis and some reactions of nitriles of N,N-bis(2-chloroethyl)-aminophenylalkanoic acids", Zh. Obshch. Khim., 1961 31 3326–3330; Chem. Abstr., 1962 57 3354e] followed by chromatography on $Al_2O_3$ grade III (elution with $CH_2Cl_2$ followed by $CH_2Cl_2$/MeOH (49:1)) afforded compound 3 of Table 1 (38% yield). Trihydrochloride salt, mp (MeOH/EtOAc) >300° C. $^1H$ NMR ($CD_3OD$) δ 8.60 (s, 1 H, H-4), 8.28 (dd, $J_{6,7}$=8.7 Hz and $J_{4,6}$=1.5 Hz, 1 H, H-6), 8.07 (d, $J_{6,7}$=8.7 Hz, 1 H, H-7), 7.78 (d, $J_{6',7'}$=9.1 Hz, 1 H, H-7'), 7.47 (dd, $J_{6',7'}$=9.1 Hz and $J_{4',6'}$=2.0 Hz, 1 H, H-6'), 7.39 (d, $J_{4',6'}$=2.0 Hz, 1 H, H-4'), 7.33 (d, $J_{2'',3''}$=8.7 Hz, 2 H, H-2'',H-6''), 6.85 (d, $J_{2'',3''}$=8.7 Hz, 2 H, H-3'',H-5''), 4.53 (s, 2 H, $ArCH_2Ar$), 4.00 (br d, J=13.7 Hz, 2 H, piperazinyl methylene), 3.80 (br t, J=6.4 Hz, 4 H, $NCH_2CH_2Cl$), 3.70 (br t, J=6.5 Hz, 6 H, $NCH_2CH_2Cl$ and piperazinyl methylene), 3.30 (m, 4 H, piperazinyl methylene), 3.01 (s, 3 H, $NCH_3$). $^{13}C$ NMR δ 158.70, 151.18, 149.04, 147.78, 135.49, 134.37, 133.13, 131.80, 127.70, 126.56, 122.07, 121.81, 120.13, 116.81, 115.75, 115.33, 114.32, 100.90, 54.60, 54.38, 48.39, 43.61, 41.52, 32.99. Fluorescence excitation $\lambda_{max}$ (MeOH) 335 nm, emission $\lambda_{max}$ (MeOH) 462 nm. Anal. ($C_{30}H_{33}N_7Cl_2.3HCl$) C,H,N.

EXAMPLE 4

Preparation of 2-[2-[2-[4-(N,N-bis(2-chloroethyl)amino)phenyl]ethyl]-5-benzimidazolyl]-5-(1-methyl-4-piperazinyl)benzimidazole (compound 4 of Table 1)

A similar reaction between (VII) and the crude imine ether hydrochloride (V, n=2) (prepared from the nitrile (IV, n=2)) [Degutis, J.; Jodelyte. A.; Sukelienne, D., "New synthesis of p-[bis(2-chloroethyl)amino]-b-phenylpropionic acid and its derivatives", Lietuvos TSR Aukstuju Mokyklu Mokslo Darbai, Chem. ir Chem. Tech., 1962 2 39–46; Chem. Abstr., 1963 59 8651a] followed by chromatography on $Al_2O_3$ (grade III) (elution with EtOAc followed by EtOAc/MeOH (33:1)) gave compound 4 of Table 1 (19% yield). Trihydrochloride salt, mp (MeOH/EtOAc) >300° C. $^1H$ NMR ($CD_3OD$) δ 8.60 (d, $J_{4,6}$=1.7 Hz, 1 H, H-4), 8.28 (dd, $J_{6,7}$=8.7 Hz and $J_{4,6}$=1.7 Hz, 1 H, H-6), 8.08 (d, $J_{6,7}$=8.7 Hz, 1 H, H-7), 7.79 (d, $J_{6',7'}$=9.1 Hz, 1 H, H-7'), 7.48 (dd, $J_{6',7'}$=9.1 Hz and $J_{4',6'}$=2.1 Hz, 1 H, H-6'), 7.39 (d, $J_{4',6'}$=2.1 Hz, 1 H, H-4'), 7.12 (d, $J_{2'',3''}$=8.7 Hz, 2 H, H-2'',H-6''), 6.72 (d, $J_{2'',3''}$=8.7 Hz, 2 H, H-3'',H 5''), 4.01 (br d, J=13.8 Hz, 2 H, piperazinyl methylene), 3.73 (br t, J=7.3 Hz, 4 H, $NCH_2CH_2Cl$), 3.69 (br d, J=12.6 Hz, 2 H, piperazinyl methylene), 3.62 (br t, J=7.3 Hz, 4 H, $NCH_2CH_2Cl$), 3.52 [t, J=7.4 Hz, 2 H, $ArCH_2CH_2C_6H_4N(CH_2CH_2Cl)_2$], 3.31 (broad m, 4H, piperazinyl methylene), 3.21 [t, J=7.3 Hz, 2 H $ArCH_2CH_2C_6H_4N(CH_2CH_2Cl)_2$], 3.01 (s, 3 H, $NCH_3$). $^{13}C$ NMR δ 158.44, 150.90, 148.98, 146.60, 135.30, 134.30, 133.00, 130.47, 128.36, 127.76, 126.25, 121.78, 120.02, 116.70, 115.78, 114.98, 113.93, 101.00, 54.54, 54.28, 48.33, 43.77, 41.74, 33.06, 30.01. Fluorescence excitation $\lambda_{max}$ (MeOH) 331 nm, emission $\lambda_{max}$ (MeOH) 449 nm. Anal. ($C_{31}H_{35}N_7Cl_2.3HCl.2H_2O$) C,H,N.

EXAMPLE 5

Preparation of 2-[2-[4-(N,N-bis(2-chloroethyl)amino)phenyl]-5-benzimidazolyl]-5-(1-methyl-4-piperazinyl)benzimidazole (compound 2 of Table 1) via the method of Scheme 2

Example of General Procedure

A solution of 4-(N,N-bis(2-chloroethyl)amino)-benzaldehyde (IX, n=0) [Anker, R. M., Cook, A. H., "Quinoxaline cyanines. Part IV. Some halogenated styryl derivatives", J. Chem. Soc., 1944 489–4927] (1.32 g, 5.4 mmol) in MeOH (25 mL) was added to a stirred solution of 2,3-diaminobenzonitrile (X) [Stephens, F. F., Bower, J. D., "The preparation of benzimindazoles and benzoxazoles from Schiff's bases. Part II.", J. Chem. Soc., 1950 1722–1726] (0.72 g, 5.4 mmol) in aqueous MeOH (25 mL), immediately followed by a 0.05M aqueous solution of cupric acetate (1.1 mol equiv.). The suspension was brought briefly to the boil and filtered hot. The precipitate was washed with aqueous MeOH and redissolved in conc. HCl. This acid solution was treated with an aqueous solution of $Na_2S$ (1.5 mol equiv.) and the precipitated CuS removed by filtration. The filtrate was then basified with conc. ammonia, diluted with water and repeatedly extracted with EtOAc. The combined organic extracts were dried ($Na_2SO_4$), filtered and concentrated, and the residue was chromatographed on $SiO_2$. Elution with $CH_2Cl_2$/EtOAc (3:1) yielded 2-[4-(N,N-bis(2-chloroethyl)amino)phenyl]-5-cyanobenzimidazole (XI, n=0) [compound 7 of Table 1] (0.80 g, 40% yield), mp (EtOAc/petroleum ether) 80° C. (dec.). $^1$H NMR (($CD_3$)$_2$CO) δ 8.15 (d, $J_{2',3'}$=9.0 Hz, 2 H, H-2',H-6'), 7.94 (d, $J_{4,6}$=1.5 Hz, 1 H, H-4), 7.69 (d, $J_{6,7}$=8.5 Hz, 1 H, H-7), 7.50 (dd, $J_{6,7}$=8.5 Hz and $J_{4,6}$=1.5 Hz, 1 H, H-6), 6.99 (d, $J_{2',3'}$=9.0 Hz, 2 H, H-3',H-5'), 3.94 (br t, J=7.5 Hz, 4 H, $NCH_2CH_2Cl$), 3.83 (br t, J=7.5 Hz, 4 H, $NCH_2CH_2Cl$). $^{13}$C NMR δ 155.98, 149.75, 143.08, 140.50, 129.62, 126.31, 120.58, 120.13, 118.40, 116.15, 112.93, 105.47, 53.52, 41.43. Anal. ($C_{18}H_{16}Cl_2N_4$) C,H,N,Cl.

Dry HCl gas was slowly bubbled into a suspension of the nitrile (XI, n=0) in dry EtOH (10 mL per mmol of nitrile) maintained at 0 to 57° C., with addition of HCl being continued until the solution became saturated. The mixture was brought to room temperature and stirred for 48 h, then concentrated under reduced pressure to give the crude imine ether hydrochloride (XII, n=0) which was employed without further purification.

A solution of 4-(1-methyl-4-piperazinyl)-1-nitroaniline (XIII) [Loewe, H.; Urbanietz, J. Basisch substituerte 2,6-bisbenzimidazolderivat, eine neue chemotherapeutisch aktive korperclasse. Arzneim-Forsch. (Drug Design), 1974 24 1927–1933] (0.40 g, 1.7 mmol) in glacial AcOH (10 mL per mmol of nitroaniline) was hydrogenated over Rh-$Al_2O_3$/Pt-C at 60 psi $H_2$ for 12 h. After this time the catalysts were removed by filtration and the resulting crude triamine (XIV) was added immediately to the imine ether hydrochloride (XII, n=0) (0.75 g, 1.7 mmol) prepared above, and the slurry was refluxed under $N_2$ for 3 h. The reaction mixture was then concentrated under reduced pressure and the crude residue was basified with conc. ammonia and then partitioned between EtOAc/water. The aqueous phase was repeatedly extracted with portions of EtOAc, and the combined organic phases were dried ($Na_2SO_4$), filtered and concentrated. Chromatography of the residue as above afforded compound 2 of Table 1 (0.75 g, 74% yield).

EXAMPLE 6

Preparation of 2-[2-[2-[4-(N,N-bis(2-chloroethyl) amino)phenyl]ethyl]-5-benzimidazolyl]-5-(1-methyl-4-piperazinyl)benzimidazole (compound 4 of Table 1)

A solution of borane dimethyl sulphide (23 mmol of a 10M solution in THF) was added slowly to a stirred solution of 3-[4-(N,N-bis(2-chloroethyl)amino)phenyl]propanoic acid (VIII, n=2) [Everett, J. L., Roberts, J. J., Ross W. C. J., "Aryl-2-halogenoalkylamines. Part XII. Some carboxylic acid derivatives of N,N-di-2-chloroethylaniline", J. Chem. Soc., 1953 2386–2392] (5.5 g, 19 mmol) in TEF (190 mL) maintained at 0° C. under a $N_2$ atmosphere. After the initial effervescence the solution was stirred for a further 4 h before being quenched with MeOH and concentrated under reduced pressure. The product was partitioned between aqueous $NaHCO_3$ and EtOAc, and the residue from the organic phase was percolated through a pad of $SiO_2$ (EtOAc elution) to give the crude alcohol, which was used without further purification. DMSO (1.15 mol equiv.) was added to a stirred solution of oxalyl chloride (1.1 mol equiv.) in THF (5 mL per mmol of alcohol) maintained at −78° C. under a $N_2$ atmosphere. Stirring was continued for 10 min after which a solution of the above alcohol (1 mol equiv.) in THF (5 mL per mmol of alcohol) was added. Stirring was continued at −78° C. for a further 15 min before $Et_3N$ (5.0 mol equiv.) was added and the mixture brought slowly to room temperature. The reaction mixture was partitioned between $H_2O$/EtOAc and the residue from the organic layer was chromatographed on $SiO_2$ and eluted with petroleum ether/ EtOAc (3:1) to give pure 3-[4-(N,N-bis(2-chloroethyl) amino]phenyl)propanal (IX, n=2) as an unstable oil (3.4 g, 68% overall yield). $^1$H NMR ($CDCl_3$) δ 9.80 (t, $J_{1,2}$=1.6 Hz, 1 H, CHO), 7.08 (d, $J_{2',3'}$=8.8 Hz, 2 H, H-2',H-6'), 6.62 (d, $J_{2',3'}$=8.8 Hz, 2 H, H-3',H-5'), 3.69 (complex t, J=6.5 Hz, 4 H, $NCH_2CH_2Cl$), 3.68 (complex t, J=6.5 Hz, 4 H, $NCH_2CH_2Cl$), 2.87 (t, $J_{2,3}$=7.4 Hz, 2 H, H-3), 2.72 (br dt, $J_{2,3}$=7.4 Hz, and $J_{1,2}$=1.6 Hz, 2 H, H2), 2.12 (complex m, 4 H, H-2). $^{13}$C NMR δ 201.88, 144.56, 129.53, 129.36, 112.28, 53.54, 45.50, 40.48, 27.04. HRMS (EI, 70 eV) : calcd. for $C_{13}H_{17}NO_3Cl_2$ 273.068720. Found: 273.06881.

The above propanal (IX, n=2) was reacted with (X) as described above, followed by chromatography on silica gel and elution with $CH_2Cl_2$/EtOAc (9:1), to give the nitrile (XI, n=2; compound 8 of Table 1) (1.6 g, 32% yield), mp (EtOAc/petroleum ether) 50° C. (dec.). $^1$H NMR (($CD_3$)$_2$CO) δ 7.95 (d, $J_{4,6}$=1.5 Hz, 1 H, H-4), 7.66 (d, $J_{6,7}$=8.4 Hz, 1 H, H-7), 7.50 (dd, $J_{6,7}$=8.4 Hz and $J_{4,6}$=1.5 Hz, 1 H, H-6), 7.12 (d, $J_{2,3}$=8.7 Hz, 2 H, H-2',H-6'), 6.70 (d, $J_{2',3'}$=8.7 Hz, 2 H, H-3',H-5'), 3.73 (m, 8 H, $NCH_2CH_2Cl$), 3.22 (br t, J=7.9 Hz, 2 H, benzylic methylene), 3.10 (br t, J=7.9 Hz, 2 H, benzylic methylene). $^{13}$C NMR δ 158.95, 145.86, 142.30, 140.28, 130.44, 130.26, 125.97, 120.69, 120.57, 116.08, 113.08, 105.27, 53.82, 41.58, 33.42, 31.96. Anal. ($C_{20}H_{20}Cl_2N_4$) C,H,N.

Conversion of (XI, n=2) to the imino ether (XII, n=2), and condensation of this with the triamine (XIV) was carried out as described above to give compound 4 of Table 1 (1.4 g, 65% yield), which had identical properties to the sample prepared by the method of Scheme 1.

EXAMPLE 7

Preparation of 2-[2-[3-[4-(N,N-bis(2-chloroethyl) amino)phenyl]propyl]-5-benzimidazolyl]-5-(1-methyl-4-piperazinyl)benzimidazole (compound 5 of Table 1)

Similar reaction of 4-[4-(N,N-bis(2-chloroethyl)-amino] phenyl)butanoic acid (VIII, n=3) [Everett, J. L., Roberts, J. J., Ross W. C. J., "Aryl-2-halogenoalkylamines. Part XII. Some carboxylic acid derivatives of N,N-di-2-chloroethylaniline", J. Chem. Soc., 1953 2386–2392] (4.75 g, 15.6 mmol) according to the above protocol gave 4[4-(N,N-bis(2-chloroethyl)amino)phenyl]butanal (IX, n=3) as a pale yellow oil (3.3 g, 73% overall yield). $^1$H NMR ($CDCl_3$) δ 9.75 (t, $J_{1,2}$=1.6 Hz, 1 H, CHO), 7.06 (d, $J_{2',3'}$=8.6 Hz, 2 H, H-2',H-6'), 6.63 (d, $J_{2',3'}$=8.6 Hz, 2 H, H-3', H-5═), 3.71 (t, J=7.4 Hz, 4 H, NCH$_2$CH$_2$Cl), 3.63 (t, J=7.4 Hz, 4 H, NCH$_2$CH$_2$Cl), 2.56 (t, J$_{3,4}$=7.4 Hz, 2 H, H-4), 2.45 (dt, J$_{2,3}$=7.3 Hz, and J$_{1,2}$=1.6 Hz, 2 H, H-2), 1.90 (quintet, J=7.4 Hz, 2 H, H-3). $^{13}$C NMR δ 202.52, 144.41, 130.28, 129.62, 112.21, 53.51, 43.10, 40.59, 33.82, 23.85. HRMS (EI, 70 eV) calcd for C$_{14}$H$_{19}$NO$^{35}$Cl$_2$: 287.08437. Found: 287.08427.

The butanal (IX, n=3) and diamine (X) were reacted together as above, followed by chromatography on silica gel and elution with CH$_2$Cl$_2$/EtOAc (5:1), to give the nitrile (XI, n=3; compound 9 of Table 1) as an oil (2.1 g, 46% yield). $^1$H NMR ((CD$_3$)$_2$CO) δ 7.94 (dd, J=0.8, 0.6 Hz, 1 H, H-4), 7.66 (dd, J$_{6,7}$=8.3, 0.6 Hz, 1 H, H-7), 7.49 (dd, J$_{6,7}$=8.3 Hz and J$_{4,6}$=1.6 Hz, 1 H, H-6), 7.10 (d, J$_{2',3'}$=8.8 Hz, 2 H, H-2',H-6'), 6.71 (d, J$_{2',3'}$=8.8 Hz, 2 H, H-3',H-5'), 3.79–3.69 (m, 8 H, NCH$_2$CH$_2$Cl), 2.97 (t, J=7.4 Hz, 2 H, ArCH$_2$CH$_2$CH$_2$C$_6$H$_4$NR$_2$), 2.64 (t, J=7.4 Hz, 2 H, ArCH$_2$CH$_2$CH$_2$C$_6$H$_4$NR$_2$), 2.15 (quintet, J=7.4 Hz, 2 H, ArCH$_2$CH$_2$CH$_2$C$_6$H$_4$NR$_2$). $^{13}$C NMR δ 159.39, 145.63, 142.28, 140.41, 131.12, 130.23, 125.91, 120.63, 120.58, 116.05, 113.11, 105.20, 53.90, 41.63, 34.77, 30.40, 29.06. Anal. (C$_{21}$H$_{22}$Cl$_2$N$_4$.H$_2$O) C,H,N.

Conversion of (XI, n=3) to the imine ether (XII, n=3) and condensation of this with (XIV) was carried out as above. Chromatography of the product on Al$_2$O$_3$ (grade V) and elution with EtOAc followed by EtOAc/MeOH (66:1) gave compound 5 of Table 1 as an orange oil (1.2 g, 41% yield). Trihydrochloride salt, mp (MeOH/EtOAc) >300° C. $^1$H NMR (CD$_3$OD) δ 8.50 (s, 1 H, H 4), 8.26 (dd, J$_{6,7}$=8.7 Hz and J$_{4,6}$=1.7 Hz, 1 H, H-6), 7.97 (d, J$_{6,7}$=8.7 Hz, 1 H, H-7), 7.83 (d, J$_{6',7'}$=9.1 Hz, 1 H, H-7'), 7.48 (dd, J$_{6,7}$=9.1 Hz and J$_{4,6}$=2.2 Hz, 1 H, H-6'), 7.44 (d, J$_{4',6'}$=2.2 Hz, 1 H, H-4'), 7.09 (d, J$_{2'',3''}$=8.6 Hz, 2 H, H-2'',H-6''), 6.52 (d, J$_{2'',3''}$=8.6 Hz, 2 H, H-3'',H-5''), 4.02 (br d, J=12.9 Hz, 2 H, piperazinyl methylene), 3.72 (br d, J=11.4 Hz, 2 H, piperazinyl methylene), 3.54 (t, J=6.0 Hz, 4 H, NCH$_2$CH$_2$Cl), 3.46 (t, J=6.0 Hz, 4 H, NCH$_2$CH$_2$Cl), 3.40–3.27 (m, 6 H, piperazinyl methylenes and ArCH$_2$CH$_2$CH$_2$C$_6$H$_4$NR$_2$), 3.03 (s, 3 H, NCH$_3$), 2.79 (t, J=6.7 Hz, 2 H, ArCH$_2$CH$_2$CH$_2$C$_6$H$_4$NR$_2$), 2.41 (quintet, J=6.3 Hz, 2 H, ArCH$_2$CH$_2$CH$_2$C$_6$H$_4$NR$_2$). $^{13}$C NMR δ 159.12, 150.93, 148.70, 145.18, 135.06, 134.19, 132.70, 130.87, 130.67, 127.59, 126.06, 121.48, 120.06, 116.46, 114.52, 113.80, 100.88, 54.59, 54.51, 48.27, 43.77, 41.73, 34.97, 28.91, 27.53. Fluorescence excitation λ$_{max}$ (MeOH) 332 nm, emission λ$_{max}$ (MeOH) 453 nm. Anal. (C$_{32}$H$_{37}$N$_7$Cl$_2$.3HCl.H$_2$O) C,H,N.

EXAMPLE 8

Preparation of 2-[2-[6-[4-(N,N-bis(2-chloroethyl) amino)phenyl]hexyl]-5-benzimidazolyl]-5-(1-methyl-4-piperazinyl)benzimidazole (compound 6 of Table 1)

Similar reaction of 7-[4-(N,N-bis(2-chloroethyl)amino) phenyl]heptanoic acid (VIII, n=6) (1.50 g, 4.34 mmol) according to the above procedure yielded 7[4-(N,N-bis(2-chloroethyl)amino)-phenyl]heptanal (IX, n=6) as an unstable colourless gum (1.34 g, 96% overall yield). $^1$H NMR (60 MHz) (CDCl$_3$) δ 9.8 (t, J$_{1,2}$=1.7 Hz, 1 H, CHO), 6.9 (d, J$_{2',3'}$=8.9 Hz, 2 H, H-2',H-6'), 6.4 (d, J$_{2',3'}$=8.9 Hz, 2 H, H-3',H-5'), 3.6 (broad s, 8 H, NCH$_2$CH$_2$Cl), 2.7–2.2 (broad m, 4 H, H-2,H-7), 1.8–0.9 (broad m, 8 H, H-3,H-4, H5.H-6). HRMS (EI, 70 eV) calcd for C$_{17}$H$_{25}$NO$^{35}$Cl$_2$ : 329.13132. Found 329.13176.

Heptanal (IX, n=6) and diamine (X) were reacted together as above, followed by chromatography on silica gel and elution with CH$_2$Cl$_2$/EtOAc (5:1), to give the nitrile (XI, n=6; compound 10 of Table 1) (0.65 g, 40% yield) as an oil. $^1$H NMR ((CD$_3$)$_2$CO) δ 7.94 (d, J$_{4,6}$=1.5 Hz, 1 H, H-4), 7.67 (d, J$_{6,7}$=8.3 Hz, 1 H, H-7), 7.50 (dd, J$_{6,7}$=8.3 Hz and J$_{4,6}$=1.5 Hz, 1 H, H-6), 7.05 (d, J$_{2',3'}$=8.7 Hz, 2 H, H-2',H-6'), 6.70 (d, J$_{2',3'}$=8.7 Hz, 2 H, H-3',H-5'), 3.78–3.68 (m, 8 H, NCH$_2$CH$_2$Cl), 2.97 (t, J=7.5 Hz, 2 H, ArCH$_2$(CH$_2$)$_5$C$_6$H$_4$NR$_2$), 2.49 (t, J=7.4 Hz, 2 H, Ar(CH$_2$)$_5$CH$_2$C$_6$H$_4$NR$_2$), 1.88 (quintet, J=7.5 Hz, 2 H, ArCH$_2$CH$_2$(CH$_2$)$_4$C$_6$H$_4$NR$_2$), 1.57 (quintet, J=7.5 Hz, 2 H Ar(CH$_2$)$_4$CH$_2$CH$_2$C$_6$H$_4$NR$_2$), 1.49–1.34 (m, 4 H, ArCH$_2$CH$_2$CH$_2$CH$_2$CH$_2$CH$_2$C$_6$H$_4$NR$_2$). $^{13}$C NMR δ 159.41, 145.46, 142.12, 140.12, 132.21, 130.24, 126.02, 120.59, 120.54, 116.04, 113.12, 105.35, 53.96, 41.65, 35.33, 32.37, 30.41, 29.76, 29.58, 29.57, 28.44. HRMS (EI, 70 eV) calcd. for C$_{24}$H$_{28}$N$_4$$^{35}$Cl$_2$ : 442.169103. Found : 442.16764.

Conversion of (XI, n=6) to the imino ether (XII, n=6) and condensation of this with IV was carried out as above. Chromatography of the product on Al$_2$O$_3$ (grade V) and elution with EtOAc followed by EtOAc/MeOH (66:1) gave compound 6 of Table 1 (0.20 g, 23% yield). Trihydrochloride salt, mp (MeOH/EtOAc) >300° C. $^1$H NMR (CD$_3$OD) δ 8.48 (d, J$_{4,6}$=1.6 Hz, 1 H, H-4), 8.17 (dd, J$_{6,7}$=8.7 Hz and J$_{4,6}$=1.6 Hz, 1 H, H-6), 8.00 (d, J$_{6,7}$=8.7 Hz, 1 H, H-7), 7.71 (d, J$_{6,7}$=9.0 Hz, 1 H, H-7'), 7.36 (dd, =9.0 Hz and J$_{4',6'}$=1.9 Hz, 1 H, H-6'), 7.32 (d, J$_{4',6'}$=1.9 Hz, 1 H, H-4'), 7.03 (d, J$_{2'',3''}$=8.5 Hz, 2 H, H-2'',H-6''), 6.75 (d, J$_{2'',3''}$=8.5 Hz, 2 H, H-3'',H-5''), 3.89 (d, J=12.4 Hz, 2 H, piperazinyl methylene), 3.66 (t, J=6.5 Hz, 4 H, NCH$_2$CH$_2$Cl), 3.59 (d, J=11.4 Hz, 2H, piperazinyl methylene), 3.52 (t, J=6.5 Hz, 4 H, NCH$_2$CH$_2$Cl), 3.28–3.10 (complex m, 6 H, piperazinyl methylenes and ArCH$_2$(CH$_2$)$_5$C$_6$H$_4$NR$_2$), 2.90 (s, 3 H, NCH$_3$), 2.45 (t, J=7.5 Hz, 2 H, Ar(CH$_2$)$_5$CH$_2$C$_6$H$_4$NR$_2$), 1.89 (quintet, J=7.5 Hz, 2 H, ArCH$_2$CH$_2$(CH$_2$)$_4$C$_6$H$_4$NR$_2$), 1.51 (quintet, J=7.1 Hz, 2 H, Ar(CH$_2$)$_4$CH$_2$CH$_2$C$_6$H$_4$NR$_2$), 1.39–1.30 (m, 4 H, ArCH$_2$CH$_2$CH$_2$CH$_2$CH$_2$C$_6$H$_4$NR$_2$). $^{13}$C NMR δ 159.16, 150.86, 148.90, 143.13, 136.04, 135.20, 134.18, 132.84, 130.73, 127.63, 126.31, 121.71, 120.02, 116.75, 115.78 (two signals superimposed), 114.99, 100.97, 55.71, 54.51, 48.31, 43.79, 41.05, 35.54, 32.17, 29.71, 29.39, 27.91, 27.70. Fluorescence excitation λ$_{max}$ (MeOH) 328 nm, emission λ$_{max}$ (MeOH) 467 nm. Anal. (C$_{35}$H$_{43}$N$_7$Cl$_2$.3HCl.4H$_2$O) C,H,N.

EXAMPLE 9

Preparation of 2-[2-[3-[4-(N-ethyl-N-(2-chloroethyl) amino)phenyl]propyl]-5-benzimidazolyl]-5-(1-methyl-4-piperazinyl)benzimidazole (compound 14 of Table 1) via the method of Scheme 3

4-[4-(N-Ethyl-N-(2-chloroethyl)amino)phenyl]-butanoic acid (XV, n=3) [Gourdie, T. A., Prakash, A. S., Wakelin, L. P. G., Woodgate, P. D., Denny, W. A., "Synthesis and evaluation of DNA-targeted spatially-separated bis(aniline) mustards as potential alkylating agents with enhanced DNA cross-linking capability", J. Med. Chem., 1991 34 240–248] was converted according to the methods in the above examples to give 4-[4-(N-ethyl-N-(2-chloroethyl)amino)-phenyl]butanal (XVI, n=3) as a colourless oil (87% overall yield). $^1$H NMR (CDCl$_3$) δ 9.22 (t, J$_{1,2}$=1.7 Hz, 1 H, CHO), 7.04 (d, J$_{2,3}$=8.7 Hz, 2 H, H-2',6'), 6.63 (d, J$_{2',3'}$=8.7 Hz, 2 H, H-3',5'), 3.59 (s, 4 H, CH$_2$CH$_2$Cl), 3.39 (q, J=7.1 Hz, 2 H, CH$_2$CH$_3$), 2.56 (t, J$_{3,4}$=7.4 Hz, 2 H, H-4), 2.44 (td, J$_{1,2}$=1.7 Hz, J$_{2,3}$=7.3 Hz, 2 H, H-2), 1.91 (quintet, J=7.4 Hz, 2 H, H-3), 1.16 (t, J=7.1 Hz, 3 H, CH$_2$CH$_3$). $^{13}$C NMR δ 202.59, 144.50, 129.42, 129.12, 52.48, 45.44, 43.16, 40.53, 33.88, 23.92, 12.49. HRMS (EI, 70 eV) calcd for C$_{14}$H$_{20}$NO$^{35}$Cl: 253.12334. Found: 253.12281.

Reaction between the butanal (XVI; n=3) and diamine (X) according to the method above gave a mixture of compounds which were dissolved in MeOH (10 mL) and stirred with KOH (10 drops, 1M) for 20 min. Usual workup followed by chromatography on silica gel and elution with $CH_2Cl_2$/EtOAc (1:1) gave first the chloroethyl nitrile (XVII, n=3; compound 11 of Table 1) (91 mg, 7%) as an oil. $^1H$ NMR ($CDCl_3$) δ 7.86 (br s, 1 H, H-4), 7.58 (dd, $J_{6,7}$=8.3 Hz and $J_{4,7}$=0.7 Hz, 1 H, H-7), 7.48 (dd, $J_{6,7}$=8.3 Hz and $J_{4,6}$=0.7 Hz, 1 H, H-6), 6.99 (d, $J_{2,3}$=8.7 Hz, 2 H, H-2',6'), 6.56 (d, $J_{2',3'}$=8.7 Hz, 2 H, H-3',5'), 3.56 (s, 4 H, $CH_2CH_2Cl$), 3.36 (q, J=7.1 Hz, 2 H, $CH_2CH_3$), 2.97 (t, J=7.4 Hz, 2 H, $ArCH_2CH_2CH_2C_6H_4NR_2$), 2.61 (t, J=7.3 Hz, 2 H, Ar $CH_2CH_2CH_2C_6H_4NR_2$), 2.16 (quintet, J=7.3 Hz, 2 H, $ArCH_2CH_2CH_2C_6H_4NR_2$), 1.13 (t, J=7.1 Hz, 3 H, $CH_2CH_3$). $^{13}C$ NMR δ 158.28, 145.36, 141.00, 137.50, 129.36, 128.66, 125.96, 119.89, 119.74, 115.17, 112.07, 105.08, 52.38, 45.39, 40.56, 34.04, 29.49, 28.50, 12.40. HRMS (EI, 70 eV) calcd for $C_{21}H_{23}N_4{}^{35}Cl$: 366.16112. Found: 366.16103. Later eluates gave the hydroxyethyl nitrile (XIX, n=3) (0.25 g, 20% overall yield) as an oil. $^1H$ NMR ($CDCl_3$) δ 7.82 (br, 1 H, H-4), 7.55 (d, $J_{6,7}$=8.3 Hz, 1 H, H-7), 7.43 (dd, $J_{6,7}$=8.3 Hz and $J_{4,6}$=1.4 Hz, 1 H, H-6), 6.87 (d, $J_{2',3'}$=8.6 Hz, 2 H, H-2',6'), 6.56 (d, $J_{2',3'}$=8.6 Hz, 2 H, H-3',5'), 3.78 (t, J=5.8 Hz, 2 H, $CH_2CH_2OH$), 3.35 (m, 4 H, $CH_2CH_2OH,CH_2CH_3$), 2.85 (t, J=7.0 Hz, 2 H, $ArCH_2CH_2CH_2C_6H_4NR_2$), 2.53 (t, J=7.0 Hz, 2 H, $ArCH_2CH_2CH_2C_6H_4NR_2$), 2.08 (m, 2 H, $ArCH_2CH_2CH_2C_6H_4NR_2$), 1.07 (t, J=7.0 Hz, 3 H, $CH_2CH_3$). $^{13}C$ NMR δ 158.73, 146.48, 146.07, 137.50, 129.08, 128.75, 125.72, 120.01, 115.15, 113.03, 111.99, 104.65, 59.71, 52.42, 45.51, 33.99, 29.61, 28.36, 11.68.

The hydroxyethyl nitrile (XIX, n=3) was converted to the corresponding imine ether hydrochloride (XX, n=3) as above, and the latter compound was reacted with (XIV) as above to give a mixture of compounds which were dissolved in MeOH (10 mL) and stirred with KOH (1 mL, 1M) for 20 min. Usual workup, followed by chromatography on alumina (grade III) and elution with EtOAc/MeOH (93:7) gave (XXI, n=3) (30% yield). $^1H$ NMR ($CD_3OD$) δ 8.18 (br s, 1 H. H-4), 7.86 (dd, $J_{6,7}$=8.5 Hz and $J_{4,6}$=1.6 Hz, 1 H, H-6), 7.59 (d, $J_{6,7}$=8.5 Hz, 1 H, H-7), 7.48 (d, $J_{6,7}$=8.8 Hz, 1 H, H-7'), 7.11 (d, $J_{4',6'}$=2.2 Hz, 1 H, H-4'), 7.01 (dd, $J_{6',7'}$=8.8 Hz and $J_{4',6'}$=2.2 Hz, 1 H, H-6'), 6.98 (d, $J_{2,3}$=8.7 Hz, 2 H, H-2',6'), 6.62 (d, $J_{2,3}$=8.7 Hz, 2 H, H-3",5"), 3.63 (t, J=6.6 Hz, 2 H, $CH_2CH_2OH$), 3.32 (m, 4 H, $CH_2CH_2OH, CH_2CH_3$), 3.19 (br t, J=4.9 Hz, 4 H, piperazinyl methylene), 2.88 (t, J=7.8 Hz, 2 H, $ArCH_2CH_2CH_2C_6H_4NR_2$), 2.64 (br t, J=4.9 Hz, 4 H, piperazinyl methylene), 2.57 (t, partially obscured, J=7.3 Hz, 2 H, $ArCH_2CH_2CH_2C_6H_4NR_2$), 2.35 (s, 3 H, $NCH_3$), 2.07 (partially resolved quintet, J=7.3 Hz, 2 H, $ArCH_2CH_2CH_2C_6H_4NR_2$), 1.07 (t, J =7.0 Hz, 3 H, $CH_2CH_3$).

A solution of the above alcohol (XXI, n=3) (92 mg, 0.17 mmol) and pyridine (0.5 mL) in dry $CH_2Cl_2$ (3 mL) was treated with excess MsCl (0.3 mL) at 0° C. The mixture was stirred for 20 min, then diluted with water and extracted with EtOAc. The combined organic extracts were washed with water, dried over anhydrous $Na_2SO_4$ and concentrated under reduced pressure to give the crude mesylate, which was treated with excess LiCl in DMF (5 mL) at 140° C. for 5 min, with rapid stirring. Excess DMF was removed under reduced pressure, and the residue was partitioned between $H_2O$/EtOAc. Workup of the organic layer and chromatography of the residue on alumina (grade III) and elution with EtOAc/MeOH (93:7) gave compound 14 of Table 1 (45 mg, 48% yield) as a yellow oil. Trihydrochloride salt, mp (MeOH/EtOAc) >300° C. $^1H$ NMR (free base in $CD_3OD$) δ 8.19 (d, $J_{4,6}$=1.6 Hz, 1 H, H-4), 7.92 (dd, $J_{6,7}$=8.4 Hz and $J_{4,6}$=1.6 Hz, 1 H, H-6), 7.59 (d, $J_{6,7}$=8.4 Hz, 1 H, H-7), 7.49 (d, $J_{6',7'}$=8.8 Hz, 1 H, H-7'), 7.12 (d, $J_{4,6}$=2.0 Hz, 1 H, H-4'), 7.01 (partially obscured dd, $J_{6',7'}$=8.8 Hz and $J_{4',6'}$=2.0 Hz, 1 H, H-6'), 6.99 (d, $J_{2",3"}$=8.6 Hz, 2 H, H-2",6"), 6.59 (d, $J_{2",3"}$=8.6 Hz, 2 H, H-3",5"), 3.54 (s, 4 H, $CH_2CH_2Cl$), 3.32 (partially obscured q, J=7.0 Hz, 2 H, $CH_2CH_3$), 3.20 (br t, J=5.0 Hz, 4 H, piperazinyl methylene), 2.88 (t, J=7.8 Hz, 2 H, $ArCH_2CH_2CH_2C_6H_4NR_2$), 2.66 (br t, J=5.0 Hz, 4 H, piperazinyl methylene), 2.58 (t, J=7.3 Hz, 2 H, $ArCH_2CH_2CH_2C_6H_4NR_2$), 2.36 (s, 3 H, $NCH_3$), 2.10 (br quintet, J=7.4 Hz, $ArCH_2CH_2CH_2C_6H_4NR_2$), 1.08 (t, J =7.0 Hz, 3 H, $CH_2CH_3$). Anal. ($C_{32}H_{38}N_7Cl.4HCl.4H_2O$) C,H,N.

EXAMPLE 10

Preparation of 2-[2-[2-[4-(N-Ethyl-N-(2-chloroethyl)amino)phenyl]ethyl]-5-benzimidazoyl]-5-(1-methyl-4-piperazinyl)benzimidazole (compound 15 of Table 1)

Similar reaction of 3-[4-(N-ethyl-N-(2-chloroethyl) amino)phenyl]propanoic acid (XV, n=2) (7.00 g, 27.4 mmol) according to the above protocol gave 3-[4-(Nethyl-N-(2-chloroethyl)amino)phenyl]propanal (XVI, n=2) as a colourless oil (5.21 g, 79% overall yield). $^1H$ NMR ($CDCl_3$) δ 9.81 (t, $J_{1,2}$=1.5 Hz, 1 H, CHO), 7.05 (d, $J_{2',3'}$=8.6 Hz, 2 H, H-2',6'), 6.63 (d, $J_{2',3'}$=8.6 Hz, 2 H, H-3',5'), 3.59 (s, 4 H, $CH_2CH_2Cl$), 3.39 (q, J=7.0 Hz, 2 H, $CH_2CH_3$), 2.86 (br t, $J_{2,3}$=7.6 Hz, 2 H, H-3), 2.72 (m, 2 H, H-2), 1.15 (t, J=7.0 Hz, 3 H, $CH_2CH_3$). $^{13}C$ NMR δ 202.10, 145.45, 129.25 (2), 128.05, 112.05 (2), 52.40, 45.56, 45.39, 40.48, 27.03, 12.43. HRMS (EI, 70 eV) calcd for $C_{13}H_{18}NO^{35}Cl$: 239.10769. Found: 239.10773.

Reaction of (XVI, n=2) with (X) as above, followed by chromatography on silica gel and elution with EtOAc/hexane (1:1), gave the chloroethyl nitrile (XVII, n=2; compound 12 of Table 1) (42% yield) as an oil. $^1H$ NMR ($CDCl_3$) δ 7.86 (br s, 1 H, H-4), 7.56 (br d, $J_{6,7}$=8.3 Hz, 1 H, H-7), 7.48 (dd, $J_{6,7}$=8.3 Hz and $J_{4,6}$=1.4 Hz, 1 H, H-6), 7.01 (d, $J_{2',3'}$=8.7 Hz, 2 H, H-2',6'), 6.59 (d, $J_{2',3'}$=8.7 Hz, 2 H, H-3',5'), 3.57 (s, 4 H, $CH_2CH_2Cl$), 3.38 (q, J=7.0 Hz, 2 H, $CH_2CH_3$), 3.24 (br t, J=7.6 Hz, 2 H, $ArCH_2CH_2C_6H_4NR_2$), 3.08 (br t, J=7.6 Hz, 2 H, Ar $CH_2CH_2C_6H_4NR_2$), 1.14 (t, J=7.0 Hz, 3 H, $CH_2CH_3$). $^{13}C$ NMR δ 157.73, 145.79, 129.26 (2), 127.45, 125.98, 119.93, 112.12 (2), 105.11, 52.31, 45.34, 40.50, 32.88, 31.41, 12.40. HRMS (EI, 70 eV) calcd for $C_{20}H_{21}N_4{}^{37}Cl$: 354.14252. Found: 354.14332.

The nitrile (XVII, n=2) was converted to the corresponding crude imine ether hydrochloride (XVIII, n=2) and this was reacted with diamine (XIV) as above, and the resulting mixture of compounds was dissolved in MeOH (60 mL) and stirred with KOH (4 mL, 1M) for 1 h. Usual workup followed by chromatography on alumina (grade III) and elution with EtOAc/MeOH (93:7) gave initially gave compound 15 of Table 1 (23% yield) as a gum. Trihydrochloride salt, mp (MeOH/EtOAc) >300° C. $^1H$ NMR (free base in $CD_3OD$) δ 8.19 (br s, 1 H, H-4), 7.91 (dd, $J_{6,7}$=8.4 Hz and $J_{4,6}$=1.2 Hz, 1 H, H-6), 7.60 (d, $J_{6,7}$=8.4 Hz, 1 H, H-7), 7.49 (d, $J_{6',7'}$=8.8 Hz, 1 H, H-7'), 7.12 (br s, 1 H, H-4'), 7.01 (partially obscured dd, $J_{4',6'}$=2.2 Hz and $J_{6',7'}$=8.8 Hz, 1 H, H-6'), 6.99 (d, $J_{2",3"}$=8.8 Hz, 2 H, H-2",6"), 6.59 (d, $J_{2",3"}$=8.8 Hz, 2 H, H-3",5"), 3.55 (br s, 4 H, $CH_2CH_2Cl$), 3.34 (q, J=7.0 Hz, 2 H, $CH_2CH_3$), 3.19 (br t, J=4.7 Hz, 4 H, piperazinyl methylene), 3.11 (m, 2 H, $CH_2CH_2C_6H_4NR_2$), 3.01 (m, 2 H, $CH_2CH_2C_6H_4NR_2$), 2.64 (br t, J=4.7 Hz, 4 H, piperazinyl methylene), 2.35 (s, 3 H, NCH$_3$), 1.08 (t, J=7.0 Hz, 3 H, CH$_2$CH$_3$). $^{13}$C NMR δ 158.48, 153.89, 149.60, 147.15, 130.28 (3), 129.61, 125.41, 122.10, 116.39, 113.59 (2), 56.19 (2), 53.64, 51.83 (2), 46.42, 46.12, 41.76, 34.48, 32.44, 12.76. Anal. (C$_{31}$H$_{36}$ClN$_7$.4HCl.H$_2$O) C,H,N,Cl.

EXAMPLE 11

Preparation of 2-[2-[6-[4-(N-ethyl-N-(2-chloroethyl) amino)phenyl]hexyl]-5-benzimidazolyl]-5-(1-methyl-4-piperazinyl)benzimidazole (compound 16 of Table 1)

Similar reaction of 7-[4-(N-ethyl-N-(2-chloroethyl) amino)phenyl]heptanoic acid (XV, n=6), (1.97 g, 6.67 mmol) gave 7-[4-(N-ethyl-N-(2-chloroethyl)amino)-phenyl] heptanal (XVI, n=6) as a colourless oil (1.40 g, 75% overall yield). $^1$H NMR (CDCl$_3$) δ 9.76 (t, J$_{1,2}$=1.6 Hz, 1 H, CHO), 7.04 (d, J$_{2',3'}$=8.7 Hz, 2 H, H-2',6'), 6.63 (d, J$_{2',3'}$=8.7 Hz, 2 H, H-3',5'), 3.59 (s, 4 H, CH$_2$CH$_2$Cl), 3.39 (q, J=7.0 Hz, 2 H, CH$_2$CH$_3$), 2.46 (br m, 4 H, H-2,7), 1.60 (br m, 4 H, H-3,6), 1.35 (br m, 4 H, H-4,H-5), 1.16 (t, J=7.0 Hz, 3 H, CH$_2$CH$_3$).; $^{13}$C NMR δ 202.83, 139.40, 130.41, 129.29, 112.05, 52.57, 45.50, 43.84, 40.57, 34.66, 31.49, 29.00, 28.90, 22.00, 12.50. HRMS (EI, 70 eV) calcd for C$_{17}$H$_{26}$NO$^{35}$Cl: 295.17029. Found: 295.17100.

A solution of the above heptanal (XVI, n=6) (100 mg, 0.36 mmol) in aqueous MeOH (20 mL) was added to a stirred solution of (X) (48 mg, 0.36 mmol) in MeOH (50 mL), immediately followed by an aqueous solution of copper (II) chloride (79 mg, 0.47 mmol) in water (10 mL). The resulting suspension was stirred and brought to reflux for 10 min, before cooling and acidifying with conc. HCl. The resulting solution was treated with a solution of Na$_2$S (129 mg, 0.54 mmol) in water (10 mL), giving an immediate brown suspension which was filtered through a pad of celite. The filtrate was then basified with conc. ammonia, diluted, and extracted with EtOAc (3×). The organic layer was washed with water, dried over anhydrous Na$_2$SO$_4$ and concentrated under reduced pressure. The residue was chromatographed on silica gel, elution with EtOAc/hexane (2:3) giving the chloroethyl nitrile (XVII, n=6; compound 13 of Table 1) (91 mg, 62% yield) as an oil. $^1$H NMR (CDCl$_3$) δ 7.91 (br s, 1 H, H-4), 7.62 (d, J$_{6,7}$=8.3 Hz, 1 H, H-7), 7.49 (dd, J$_{6,7}$=8.3 Hz and J$_{4,6}$=1.4 Hz, 1 H, H-6), 6.97 (d, J$_{2',3'}$=8.6 Hz, 2 H, H-2',6'), 6.62 (d, J$_{2',3'}$=8.6 Hz, 2 H, H-3',5'), 3.58 (s, 4 H, CH$_2$CH$_2$Cl), 3.38 (q, J=7.0 Hz, 2 H, CH$_2$CH$_3$), 2.99 (t, J=7.8 Hz, 2 H, ArCH$_2$(CH$_2$)$_5$C$_6$H$_4$NR$_2$), 2.45 (t, J=7.7 Hz, 2 H, Ar(CH$_2$) CH$_2$C$_6$H$_4$NR$_2$), 1.89 (quintet, J=7.8 Hz, 2 H, ArCH$_2$CH$_2$(CH$_2$)$_4$C$_6$H$_4$NR$_2$), 1.45 (br m, 6 H, ArCH$_2$CH$_2$(CH$_2$)$_3$CH$_2$C$_6$H$_4$NR$_2$), 1.15 (t, J=7.0 Hz, 3 H, CH$_2$CH$_3$). $^{13}$C NMR δ 158.38, 144.89, 140.37, 137.80, 129.28, 126.17, 124.26, 119.75, 115.20, 112.20, 105.39, 54.63, 52.58, 45.59, 40.54, 34.60, 31.40, 29.10, 28.77, 27.86, 12.45. HRMS (EI, 70 eV) calcd for C$_{24}$H$_{29}$N$_4$$^{37}$Cl 410.20512. Found 410.20644.

The above nitrile (XVII, n=6) was converted to the corresponding crude imine ether hydrochloride (XVIII, n=6), and this was reacted with (XIV) as above to give a mixture of compounds which were dissolved in MeOH (10 mL) and stirred with KOH (1 mL, 1M) for 20 min. Usual workup followed by chromatography on alumina (grade III) and elution with EtOAc/MeOH (93:7) gave initially the chloroethyl bisbenzimidazole (compound 16 of Table 1) (36 mg, 5% yield) as a gum. Trihydrochloride salt, mp (MeOH/EtOAc) >300° C. $^1$H NMR (free base in CD$_3$OD) δ 8.21 (d, J$_{4,6}$=1.6 Hz, 1 H, H-4), 7.93 (dd, J$_{6,7}$=8.5 Hz and J$_{4,6}$=1.6 Hz, 1 H, H-6), 7.60 (d, J$_{6,7}$=8.5 Hz, 1 H, H-7), 7.48 (d, J$_{6,7}$=8.8 Hz, 1 H, H-7'), 7.10 (d, J$_{4,6}$=2.0 Hz, 1 H, H-4'), 6.98 (dd, J$_{4',6'}$=2.0 Hz and J$_{6',7'}$=8.8 Hz, 1 H, H-6'), 6.89 (d, J$_{2,3}$=8.7 Hz, 2 H, H-2'',6''), 6.54 (d, J$_{2,3}$=8.7 Hz, 2 H, H-3'',5''), 3.52 (s, 4 H,CH$_2$CH$_2$Cl), 3.33 (partially obscured q, J=7.0 Hz, 2 H, CH$_2$CH$_3$), 3.17 (br t, J=4.6 Hz, 4 H, piperazinyl methylene) 2.84 (t, J=7.3 Hz, 2 H, ArCH$_2$(CH$_2$) $_5$C$_6$H$_4$NR$_2$), 2.64 (br t, J=4.6 Hz, 4 H, piperazinyl methylene), 2.39 (partially obscured t, J=7.2 Hz, Ar(CH$_2$) $_5$CH$_2$C$_6$H$_4$NR$_2$), 2.35 (s, 3 H, NCH$_3$), 1.79 (quintet, J=7.3 Hz, 2 H, ArCH$_2$CH$_2$(CH$_2$)$_4$C$_6$H$_4$NR$_2$), 1.40 (br m, 6 H, ArCH$_2$CH$_2$(CH$_2$)$_3$CH$_2$C$_6$H$_4$NR$_2$), 1.05 (t, J =7.0 Hz, 3 H, CH$_2$CH$_3$) Anal. (C$_{35}$H$_{44}$ClN$_7$.4HCl.10H$_2$O) C,H,N,Cl. Later eluates gave the hydroxyethyl bisbenzimidazole (XXI, n=6) (178 mg, 28% yield). $^1$H NMR(CD$_3$OD) δ 8.21 (d, J$_{4,6}$=1.5 Hz, 1 H, H-4), 7.94 (dd, J$_{6,7}$=8.4 Hz, 1 H, H-6), 7.62 (d, J$_{6,7}$=8.4 Hz, 1 H, H-7), 7.50 (d, J$_{6',7'}$=8.8 Hz, 1 H, H-7'), 7.13 (d, J$_{4',6'}$=1.9 Hz, 1 H, H-4'), 7.0 (dd, J$_{6',7'}$=8.8 Hz and J$_{4,6}$=1.9 Hz, 1 H, H-6'), 6.91 (d, J$_{2,3}$=8.6 Hz, 2 H, H-2'',6''), 6.60 (d, J$_{2'',3''}$=8.6 Hz, 2 H, H-3'',5''), 3.64 (t, J=6.3 Hz, 2 H, CH$_2$CH$_2$OH), 3.33 (m, 4 H, CH$_2$CH$_2$OH, CH$_2$CH$_3$), 3.21 (br t, J=5.1 Hz, 4 H, piperazinyl methylene, 2.88 (t, J=7.6 Hz, 2 H, ArCH$_2$(CH$_2$)$_5$C$_6$H$_4$NR$_2$), 2.66 (br t, J=5.1 Hz, 4 H, piperazinyl methylene), 2.43 (partially obscured t, J=7.1 Hz, 2 H, Ar(CH$_2$)$_5$CH$_2$C$_6$H$_4$NR$_2$), 2.36 (s, 3 H, NCH$_3$), 1.83 (br quintet, J=7.6 Hz, 2 H, ArCH$_2$CH$_2$(CH$_2$)$_4$C$_6$H$_4$NR$_2$), 1.45 (br m, 6 H, ArCH$_2$CH$_2$(CH$_2$)$_3$CH$_2$C$_6$H$_4$NR$_2$), 1.07 (t, J=7.0 Hz, 3 H, CH$_2$CH$_3$).

The hydroxyethyl compound (XXI, n=6) was converted back to the chloroethyl bisbenzimidazole (compound 16 of Table 1) as described above.

EXAMPLE 12

Preparation of 2-[2-[[4-(N-ethyl-N-(2-chloroethyl) amino)phenyl]methyl]-5-benzimidazoyl]-5-(1-methyl-4-piperazinyl)benzimidazole (compound 17 of Table 1) via the method of Scheme 4

Example of General Procedure

The phenylenediamine (VII) (1.34 g, 4.14 mmol) was prepared by catalytic hydrogenation (60 psi, 12 h) of the corresponding nitroaniline (VI) in MeOH/EtOAc (1:2) over Pt-C/Rh-Al$_2$O$_3$. The filtered hydrogenation solution was concentrated in vacuo and then 2-[4-(N-ethyl-N-(2-chloroethyl)amino)phenyl]acetic acid (XV, n=1) (1.00 g, 4.14 mmol) was added, followed by a solution of PPE, as prepared in CHCl$_3$/Et$_2$O [Fieser and Fieser, Reagents for Organic Synthesis, Vol. 1, p, 892, John Wiley and Sons Inc., 1967]. Solvents were removed under reduced pressure, and the resulting syrup was heated at 100° C. for 2 h on an oil bath. The cooled mixture was dissolved in MeOH, diluted with water and basified with conc. ammonia, then extracted with EtOAc (3×). The combined organic extracts were washed with water, dried over anhydrous Na$_2$SO$_4$ and concentrated under redcued pressue, and the residue was chromatographed on alumina (grade III). Elution with EtOAc/MeOH (95:5) gave compound 17 of Table 1 (0.82 g, 38%) as a yellow oil. Trihydrochloride salt, mp (MeOH/EtOAc) >300° C. $^1$H NMR (free base in CD$_3$OD) δ 8.18 (br s, 1 H, H-4), 7.91 (dd, J$_{6,7}$=8.5 Hz and J$_{4,6}$=1.6 Hz, 1 H, H-6), 7.58 (d, J$_{6,7}$=8.5 Hz, 1 H, H-7), 7.46 (d, J$_{6',7'}$=8.8 Hz, 1 H, H-7'), 7.12 (d, J$_{2'',3''}$=8.8 Hz, 2 H, H-2'',6''), 7.08 (d, J$_{4,6}$=2.3 Hz, 1 H, H-4'), 6.98 (dd, J$_{6'}$,7'=8.8 Hz and J$_{4',6'}$=2.3 Hz, 1 H, H-6'), 6.61 (d, J$_{2'',3''}$=8.8 Hz, 2 H, H-3'',5''), 4.08 (s, 2 H, ArCH$_2$Ar), 3.53 (s, 4 H, CH$_2$CH$_2$Cl), 3.32 (q, J=6.9 Hz, 2 H, CH$_2$CH$_3$), 3.16 (br t, J=4.6 Hz, 4 H, piperazinyl methylene), 2.61 (br t, J=4.6 Hz, 4 H, piperazinyl methylene), 2.32 (s, 3 H, NCH$_3$), 1.05 (t, J=7.0 Hz, 3 H, CH$_2$CH$_3$). $^{13}$C NMR δ 158.28, 153.81, 149.53, 147.58, 140.10, 136.00, 130.86 (2), 125.43, 125.36, 122.16, 116.60, 116.33, 113.53 (2), 102.28, 56.12 (2), 53.47, 51.73 (2), 46.33, 46.07, 41.69, 35.29, 12.71. Anal. (C$_{30}$H$_{34}$N$_7$Cl.3HCl.3H$_2$O) C,H,N.

EXAMPLE 13

Preparation of 2-[2-[3-[3-(N,N-bis(2-chloroethyl)] amino)phenyl]propyl]-5-benzimidazolyl]-5-(1-methyl-4-piperazinyl)benzimidazole (compound 18 of Table 1)

To a mixture of m-chlorambucil (XXII) (1.00 g, 3.29 mmol) [Palmer, B. P., Wilson, W. R., Denny, W. A., "Nitro analogues of chlorambucil as potential hypoxia-selective anti-tumour drugs", Anti-Cancer Drug Design, 1990 5, 337–349] and freshly prepared diamine (VII) (4.00 mmol, 1.30 g) was added PPE solution (40 mL). The method described above was followed to give compound 18 of Table 1 (0.73 g, 38% yield) as a white powder, mp ca 220° C. (decomp.). $^1$H NMR (CD$_3$OD) δ 8.19 (br s, 1 H, H-4), 7.92 (dd, J$_{6,7}$=8.4 Hz and J$_{4,6}$=1.1 Hz, 1 H, H-6), 7.59 (d, J$_{6,7}$=8.2 Hz, 1 H, H-7), 7.48 (d, J$_{6',7'}$=8.8 Hz, 1 H, H-7'), 7.11 (partially obscured s, 1 H, H-4'), 7.10 (t, J=7.8 Hz, 1H, H-5"), 7.00 (dd, J$_{6',7'}$=8.8 Hz and J$_{4',6'}$=2.3 Hz, 1 H, H-6'), 6.57–6.50 (m, 3H, H-2",4",6"), 3.69–3.58 (m, 8H, N(CH$_2$CH$_2$Cl)$_2$), 3.18 (br t, J=4.9 Hz, 4H, piperazinyl methylene), 2.91 (t, J=7.8 Hz, 2H, ArCH$_2$CH$_2$CH$_2$C$_6$H$_4$NR$_2$), 2.64 (partially obscured t, J=7.6 Hz, 2H, ArCH$_2$CH$_2$CH$_2$C$_6$H$_4$NR$_2$), 2.62 (br t, J=5.2 Hz, 4H, piperazinyl methylene), 2.33 (s, 3H, NCH$_3$), 2.15 (quintet, J=7.6 Hz, 2H, ArCH$_2$CH$_2$CH$_2$C$_6$H$_4$NR$_2$). $^{13}$C NMR δ 158.77, 153.84, 149.57, 147.86, 144.06, 130.65, 125.39, 122.08, 118.78, 116.37, 113.45, 111.11, 56.16 (×2), 54.40 (×2), 51.80 (×2), 46.12, 41.71 (×2), 38.85, 30.84, 29.46. Anal. (C$_{32}$H$_{37}$N$_7$Cl$_2$.1$^{.5}$H$_2$O) C,H,N,Cl.

EXAMPLE 14

Preparation of 2-[2-[3-[3-(N-ethyl-N-(2-chloroethyl) amino)phenyl]propyl]-5-benzimidazolyl]-5-(1-methyl-4-piperazinyl)-benzimidazole (compound 19 of Table 1)

To a mixture of m-chlorambucil half mustard (XXIII) (0.75 g, 2.78 mmol) and freshly prepared diamine (VII) (3.01 mmol, 0.97 g) was added PPE solution (40 mL). The method described above was followed to give compound 19 of Table 1 (1.05 g, 73% yield) as a white powder, mp ca 220° C. (decomp.). $^1$H NMR (CD$_3$OD) δ 8.19 (br s, 1 H, H-4), 7.92 (dd, J$_{6,7}$=8.4 Hz and J$_{4,6}$=1.4 Hz, 1 H, H-6), 7.59 (br d, J$_{6,7}$=8.2 Hz, 1 H, H-7), 7.47 (d, J$_{6,7}$=8.8 Hz, 1 H, H-7'), 7.11 (br s, 1 H, H-4'), 7.07 (t, J=8.4 Hz, 1H, H-5"), 6.99 (dd, J$_{6',7'}$=8.8 Hz and J$_{4',6'}$=2.1 Hz, 1 H, H-6'), 6.52–6.48 (m, 3H, H-2", 4", 6"), 3.57 (s, 4H, CH$_2$CH$_2$Cl), 3.37 (q, J=7.0 Hz, 2H, CH$_2$CH$_3$), 3.18 (br t, J=4.9 Hz, 4H, piperazinyl methylene), 2.91 (t, J=7.8 Hz, 2H, ArCH$_2$CH$_2$CH$_2$C$_6$H$_4$NR$_2$), 2.63 (m, 6H, ArCH$_2$CH$_2$CH$_2$C$_6$H$_4$NR$_2$, piperazinyl methylene), 2.33 (s, 3, NCH$_3$), 2.15 (quintet, J=7.7 Hz, 2H, ArCH$_2$CH$_2$CH$_2$C$_6$H$_4$NR$_2$), 1.09 (t, J=7.0 Hz, 3, CH$_2$CH$_3$). $^{13}$C NMR δ 158.82, 153.86, 149.59, 148.68, 143.74, 130.44, 125.40, 122.25, 117.92, 116.38, 113.45, 111.14, 56.17 (×2), 53.53, 51.81 (×2), 46.33, 46.12, 41.78, 36.93, 30.93, 29.50, 12.81. Anal. (C$_{32}$H$_{38}$N$_7$Cl ) C,H,N,Cl.

EXAMPLE 15

Preparation of 2-[2-[3-[2-(N,N-bis(2-chloroethyl) aminophenyl]propyl]-5-benzimidazolyl]-5-(1-methyl-4-piperazinyl)-benzimidazole (compound 20 of Table 1)

To a mixture of o-chlorambucil (XXIV) (1.00 g, 3.29 mmol) and freshly prepared diamine (VII) (4.00 mmol, 1.30 g) was added PPE solution (40 mL). The method described above was followed to give compound 20 of Table 1 (1.27 g, 65% yield) as a white powder, mp ca 230° C. (decomp.). $^1$H NMR (CD$_3$OD) δ 8.22 (br s, 1 H, H-4), 7.94 (dd, J$_{6,7}$8.5 Hz and J$_{4,6}$=1.3 Hz, 1 H, H-6), 7.63 (d, J$_{6,7}$=8.3 Hz, 1 H, H-7), 7.49 (d, J$_{6',7'}$=8.8 Hz, 1 H, H-7'), 7.29–7.07 (m, 5H, H-4', 3", 4", 5", 6"), 7.01 (dd, J$_{4',6'}$=2.2 Hz and J$_{6',7'}$=8.8 Hz, 1H, H-6'), 3.38 (br t, J=6.5 Hz, 4H, CH$_2$CH$_2$Cl), 3.25 (br t, J=6.8 Hz, 4H, CH$_2$CH$_2$Cl), 3.19 (br t, J=4.9 Hz, 4H, piperazinyl methylene), 2.97 (t, J=7.5 Hz, 2H, ArCH$_2$CH$_2$CH$_2$C$_6$H$_4$NR$_2$), 2.84 (br t, J=7.8 Hz, 2H, ArCH$_2$CH$_2$CH$_2$C$_6$H$_4$NR$_2$), 2.63 (br t, J=4.7 Hz, 4H, piperazinyl methylene), 2.34 (s, 3, NCH$_3$), 2.15 (quintet, J=7.6 Hz, 2H, ArCH$_2$CH$_2$CH$_2$C$_6$H$_4$NR$_2$). $^{13}$C NMR δ 158.80, 153.89, 149.58, 149.12, 140.72, 130.99, 128.13, 126.66, 125.48, 125.42, 122.15, 116.38, 58.11 (×2), 56.17 (×2), 51.80 (×2), 46.11, 42.56 (×2), 30.77, 30.29, 29.99. Anal. (C$_{32}$H$_{37}$N$_7$Cl$_2$) C,H,N,Cl.

EXAMPLE 16

Preparation of 2-[2-[3-[2-(N-ethyl-N-(2chloroethyl) amino)phenyl]propyl]-5-benzimidazolyl]-5-(1-methyl-4-piperazinyl)-benzimidazole (compound 21 of Table 1)

To a mixture of o-chlorambucil half mustard (XXV) (0.75 g, 2.78 mmol) and freshly prepared diamine (VII) (3.01 mmol, 0.97 g) was added PPE solution (40 mL). The method described above was followed to give compound 21 of Table 1 (0.74 g, 48% yield) as a white powder, mp ca 220° C. (decomp.). $^1$H NMR (CD$_3$OD) δ 8.22 (br s, 1 H, H-4), 7.94 (dd, J$_{6,7}$=8.5 Hz and J$_{4,6}$=1.4 Hz, 1 H, H-6), 7.62 (d, J$_{6,7}$ =8.3 Hz, 1 H, H-7), 7.49 (d, J$_{6',7'}$=8.8 Hz, 1 H, H-7'), 7.25–7.00 (m, 6H, H-4', 6', 3", 4", 5", 6"), 3.37 (t, J=6.8 Hz, 2H, NCH$_2$CH$_2$Cl), 3.18 (m, 6H, ArCH$_2$CH$_2$CH$_2$CH$_4$NR$_2$, piperazinyl methylene ), 2.95 (br t, J=7.4 Hz, 2H, NCH$_2$CH$_2$Cl), 2.90 (q, J=7.1 Hz, 2H, CH$_2$CH$_3$), 2.82 (br t, J=8.1 Hz, 2H, ArCH$_2$CH$_2$CH$_2$C$_6$H$_4$NR$_2$), 2.64 (br t, J=4.5 Hz, 4H, , piperazinyl methylene), 2.34 (s, 3, NCH$_3$), 2.14 (quintet, J=7.7 Hz, 2H, ArCH$_2$CH$_2$CH$_2$C$_6$H$_4$NR$_2$), 0.89 (t, J=7.0 Hz, 3, CH$_2$CH$_3$). $^{13}$C NMR δ 158.89, 153.89, 150.20, 149.59, 140.57, 130.89, 127.88, 126.00, 125.41, 124.53, 122.09, 116.38, 57.13, 56.18 (×2), 51.81 (×2), 50.60, 46.11, 42.59, 31.07, 30.34, 29.98, 13.05. Anal. (C$_{32}$H$_{38}$N$_7$Cl) C,H, N,Cl.

EXAMPLE 17

Preparation of compounds 22 and 23 of Table 1 via the method of Scheme 5

To a solution of SOCl$_2$ (60 mL) in dry EtOH (300 mL) was added 4,5-imidazoledicarboxylic acid (XXVI) (12.6 g, 80.7 mmol). The resulting suspension was heated under reflux for 18 h, by which time it had cleared, it was then cooled and concentrated in vacuo to give a crude white solid. The solid was dissolved in EtOAc, washed with dil. ammonia, water and brine and then dried over anhydrous Na$_2$SO$_4$ and concentrated under reduced pressure to give (XXVII) (12.3 g, 72% yield), mp 153–159° C. [Bauer, L., Namburg, C. N. V., Dhawan, D., J. Heterocyc. Chem., 1964 1 275–278 report mp 151–152° C]. $^1$H NMR (CDCl$_3$) δ 7.91 (s, 1 H, H-2), 4.39 (q, J=7.1 Hz, 4 H, CH$_2$CH$_3$), 1.36 (t, J=7.1 Hz, 6 H, CH$_2$CH$_3$).

To a solution of (XXVII) (6.00 g, 28.3 mmol) in dry DMF (50 mL) was added anhydrous K$_2$CO$_3$ (1.1 mol eq, 4.30 g) and tert butyl-4-bromobutyrate (1.3 mol eq, 8.20 g)

(XXVIII). The resulting mixture was heated at 100° C. with vigorous stirring under $N_2$ for 1 h, after which time the DMF was evaporated under reduced pressure. The residue was then partitioned between water and EtOAc, and the residue from usual workup of the organic layer was chromatographed on silica gel. Elution with EtOAc/hexane (7:3) gave the N-alkylated imidazole (XXIX) (7.90 g, 79% yield) as a colourless oil. $^1$H NMR (CDCl$_3$, 200 MHz) δ 7.52 (s, 1 H, H2), 4.36 (q, J=7.1 Hz, 4 H, CH$_2$CH$_3$), 4.27 (t, J=7.0 Hz, 2 H, NCH$_2$), 2.21 (t, J=6.7 Hz, 2H, CH$_2$COO$^t$Bu), 2.03 (m, 2 H, CH$_2$CH$_2$CH$_2$), 1.44 (s, 9H, C(CH$_3$)$_3$), 1.38 (t, J=7.1 Hz, 3 H, CH$_2$CH$_3$), 1.36 (t, J=7.1 Hz, 3 H, CH$_2$CH$_3$).

A solution of the ester (XXIX) (3.60 g, 10.2 mmol) in formic acid (80 mL) was stirred overnight with a drying tube, then warmed to 50° C. and stirred for 4 h until reaction was complete by tlc. The solvent was removed under reduced pressure and the crude product was partitioned between EtOAc and water, the organic layer was washed with water and brine then dried over anhydrous Na$_2$SO$_4$ and concentrated in vacuo to give a white solid which was recrystalised from toluene/hexane to give the carboxylic acid (XXX) (2.77 g, 91% yield) as white crystals, mp 78–80° C. $^1$H NMR (CDCl$_3$) δ 10.49 (br s, 1 H, COOH), 7.76 (s, 1 H, H-2), 4.39 (q, J=7.0 Hz, 2 H, CH$_2$CH$_3$), 4.37 (q, J=7.0 Hz, 2 H, CH$_2$CH$_3$), 4.33 (t, J=7.1 Hz, 2 H, NCH$_2$), 2.38 (t, J=6.9 Hz, 2 H, CH$_2$COOH), 2.12 (quintet, J=7.0 Hz, 2H, CH$_2$CH$_2$CH$_2$), 1.38 (t, J=7.0 Hz, 3 H, CH$_2$CH$_3$), 1.37 (t, J=7.0 Hz, 3 H, CH$_2$CH$_3$); $^{13}$C NMR δ 176.00, 162.05, 159.75, 139.80, 136.59, 124.51, 61.83, 61.32, 46.21, 30.34, 25.89, 14.05, 13.84. Anal. (Cl$_3$H$_{18}$N$_2$O$_6$) C,H,N.

A solution of the carboxylic acid (1.50 g, 4.62 mmol) in neat SOCl$_2$ (10 mL) with one drop of DMF added, was stirred at r.t. for 1 h, after which time the excess SOCl$_2$ was distilled off under reduced pressure and dry benzene was added and then removed in vacuo to ensure all traces of SOCl$_2$ had been removed. The crude acid chloride was then dissolved in dry THF (20 mL) and added dropwise via cannula to a solution of the nitroaniline (XIII) (2.0 mol eq, 9.25 mmol, 2.20 g) in dry THF (30 mL) under $N_2$. The addition is accompanied by formation of a yellow precipitate which is presumably the HCl salts of the nitroaniline and product amide. The reaction was stirred for 2 h and then diluted with sat. NaHCO$_3$ and extracted with EtOAc. The combined organic extracts were washed with water and brine, then dried over anhydrous Na$_2$SO$_4$ and concentrated in vacuo. Column chromatography on alumina (grade III) and elution with EtOAc gave recovered nitroaniline (XIII) (0.80 g), further elution with EtOAc/MeOH (97:3) gave the amide (XXXI) (1.88 g, 79% yield) as a yellow oil which crystalised on standing, mp 66–68° C. $^1$H NMR (CDCl$_3$) δ 11.05 (s, 1H, NHCO), 8.28 (d, J$_{4,6}$=2.9 Hz, 1H, H-4), 8.14 (d, J$_{6,7}$=9.7 Hz, 1H, H-7), 7.62 (s, 1H, H-2'), 6.55 (dd, J$_{4,6}$=2.9 Hz and J$_{6,7}$=9.7 Hz, 1H, H-6), 4.38 (m, 6H, CH$_2$CH$_3$ ×2, CH$_2$N), 3.51 (t, J=3.5 Hz, 4H, piperazinyl methylene), 2.54 (m, 6H, piperazinyl methylene, NHCOCH$_2$), 2.35 (s, 3, NCH$_3$), 2.23 (quintet, J=7.2 Hz, 2H, CH$_2$CH$_2$CH$_2$), 1.39 (t, J=7.1 Hz, 3, CH$_2$CH$_3$), 1.38 (t, J=7.1 Hz, 3, CH$_2$CH$_3$). $^{13}$C NMR δ 170.77, 162.59, 160.01, 155.46, 139.59, 137.82, 137.49, 128.53, 125.99, 124.23, 107.86, 102.70, 61.73, 61.26, 54.41 (×2), 46.53 (×2), 46.01, 45.92, 34.56, 26.19, 14.16, 13.91. Anal. (C$_{24}$H$_{32}$N$_6$O$_7$) C,H,N.

A solution of the amide (XXXI) (1.28 g, 2.48 mmol) in dry EtOH (50 mL) was hydrogenated (60 psi) over a mixed catalyst system comprising of Pt-C and Rh-Al$_2$O$_3$ until the solution was colourless (ca. 8 h). The solution was then filtered through celite and cooled to 0° C. HCl (g) was bubbled directly into the solution for 5 min and then the solution was warmed to 70° C. for 24 h, after which time the solvent was removed at reduced pressure, the residue was diluted with water, basified by the addition of dil. ammonia and EtOAc extracted several times. The combined organic extracts were washed with water and brine, then dried over anhydrous Na$_2$SO$_4$ and concentrated in vacuo. Column chromatography on alumina (grade III) and gradient elution with EtOAc to MeOH/EtOAc (9:1) gave the benzimidazole (XXXII) (0.99 g, 85% yield) as a white powder, mp 122–124° C. $^1$H NMR (CDCl$_3$) δ 10.96 (br s, 1H, NH), 7.53 (s, 1H, H-2'), 7.44 (br s, 1H, H-7), 7.02 (br s, 1H, H-4), 6.94 (dd, J$_{4,6}$=2.2 Hz and J$_{6,7}$=8.8 Hz, 1H, H-6), 4.32 (m, 6H, CH$_2$CH$_3$ ×2, CH$_2$N), 3.17 (t, J=5.0 Hz, 4H, piperazinyl methylene), 2.83 (t, J=7.0 Hz, 2H, CH$_2$CH$_2$CH$_2$N), 2.61 (t, J=4.9 Hz, 4H, piperazinyl methylene), 2.36 (s, 3, NCH$_3$), 2.35 (partially obscured quintet, J=7.1 Hz, 2H, CH$_2$CH$_2$CH$_2$), 1.33 (t, J=7.1 Hz, 3, CH$_2$CH$_3$), 1.32 (t, J=7.1 Hz, 3, CH$_2$CH$_3$). $^{13}$C NMR δ 162.69, 159.99, 152.17, 148.01, 139.69, 137.24, 124.67, 114.43, 61.90, 61.37, 55.19 (×2), 50.94, 46.11 (×2), 46.01, 28.39, 25.36, 14.08, 13.87. Anal. (C$_{24}$H$_{32}$N$_6$O$_4$) C,H,N.

To a slurry of LiAlH$_4$ (4 mol eq, 6.06 mmol, 0.23 g) in dry THF (5 mL) at 0° C. under $N_2$ was added dropwise a solution of the diester (XXXII) (0.71 g, 1.52 mmol) in dry THF (20 mL). After addition was complete the reaction was stirred for 2 h and then water (~2 mL) and 5M NaOH (~2 mL) were alternately added dropwise until the excess LiAlH$_4$ had been quenched. The resulting suspension was filtered through a pad of celite which was washed with hot THF. The celite and lithium salts were then soxhlet extracted with THF for 20 h and then the combined filtrate and soxhlet extraction were concentrated at reduced pressure to give a crude white solid which was recrystalised from MeOH/EtOAc to give compound 22 of Table 1 (0.35 g, 60% yield), as a white powder, mp 197–200° C. $^1$H NMR (CD$_3$OD) δ 7.64 (s, 1H, H-2'), 7.38 (d, J$_{6,7}$=8.8 Hz, 1H, H-7), 7.04 (br s, 1H, H-4), 6.97 (dd, J$_{4,6}$=2.1 Hz and J$_{6,7}$=8.8 Hz, 1H, H-6), 4.64 (s, 2H, CH$_2$OH), 4.52 (s, 2H, CH$_2$OH), 4.14 (t, J=7.2 Hz, 2H, CH$_2$N), 3.16 (t, J=4.8 Hz, 4H, piperazinyl methylene), 2.88 (t, J=7.4 Hz, 2H, CH$_2$CH$_2$CH$_2$N), 2.64 (t, J=4.8 Hz, 4H, piperazinyl methylene), 2.35 (s, 3, NCH$_3$), 2.34 (partially obscured quintet, J=7.3 Hz, 2H, CH$_2$CH$_2$CH$_2$). $^{13}$C NMR δ 154.94, 149.30, 140.03, 139.50, 138.36, 135.35, 129.91, 116.00, 115.98, 102.42, 57.50, 56.17 (×2), 52.77, 51.93 (×2), 46.10, 45.43, 30.12, 26.69. Anal. (C$_{20}$H$_{28}$N$_6$O$_2$.H$_2$O) C,H,N.

To a suspension of the diol (compound 22 of Table 1) (155 mg, 0.403 mmol) in dry CH$_2$Cl$_2$ (8 mL) was added methyl isocyanate (2.5 mol eq, 1.01 mmol, 42 mL) and dibutyl tin diacetate (2 drops). The suspension was stirred for 12 h and then a further two 80 mL portions of methyl isocyanate were added over 8 h. The reaction mixture cleared and appeared to be complete by tlc, after which it was put directly onto an alumina (grade III) column and chromatographed with gradient elution from EtOAc to MeOH/EtOAc (9:1) to give compound 23 of Table 1 (115 mg, 57% yield) as a white powder, mp 168–169° C. $^1$H NMR (CDCl$_3$) δ 7.42 (partially obscured d, J$_{6,7}$=8.8 Hz, 1H, H-7), 7.41 (s, 1H, H-2'), 7.01 (br s, 1H, H-4), 6.93 (dd, J$_{4,6}$=2.2 Hz and J$_{6,7}$=8.8 Hz, 1H, H-6), 5.78 (q, J=4.5 Hz, 1H, CH$_3$NHCO), 5.13 (s, 2H, CH$_2$OCONHCH$_3$), 5.06 (s, 2H, CH$_2$OCONHCH$_3$), 4.98 (q, J=4.6 Hz, 1H, CH$_3$NHCO), 4.02 (t, J=6.8 Hz, 2H, CH$_2$N), 3.16 (t, J=4.7 Hz, 4H, piperazinyl methylene), 2.78 (t, J=7.4 Hz, 2H, CH$_2$CH$_2$CH$_2$N), 2.73 (d, J=4.7 Hz, 3, CH$_3$NHCO), 2.69 (d, J=4.7 Hz, 3, CH$_3$NHCO), 2.61 (t, J=4.9 Hz, 4H, piperazinyl methylene), 2.36 (s, 3, NCH$_3$), 2.32 (quintet, J=7.2 Hz, 2H, $CH_2CH_2CH_2$). $^{13}C$ NMR δ 157.07 (×2), 156.64, 152.70, 148.10, 137.84, 137.33, 125.37, 114.49, 101.30, 59.40, 55.22 (×2), 54.23, 50.94 (×2), 46.03, 44.52, 28.60, 27.48 (×2), 25.67. Anal. ($C_{24}H_{34}N_8O_4$) C,H,N.

EXAMPLE 18

Preparation of compounds 24 and 25 of Table 1 via the method of Scheme 6

To a mixture of carboxylic acid (XXX) (2.68 g, 8.26 mmol) and freshly prepared diamine (VII) (0.98 mol eq, 8.12 mmol, 2.62 g) was added PPE solution (90 mL). The method above (Example 12) was followed to give the bisbenzimidazole (XXXIII) (1.94 g, 41% yield) as an orange powder, mp 143–149° C. $^1H$ NMR ($CD_3OD$) δ 8.19 (d, $J_{4,6}$=1.6 Hz, 1 H, H-4), 7.92 (dd, $J_{6,7}$=8.4 Hz and $J_{4,6}$=1.6 Hz, 1 H, H-6), 7.91 (s, 1H, H-2'), 7.61 (d, $J_{6,7}$=8.4 Hz, 1 H, H-7), 7.48 (d, $J_{6',7'}$=8.8 Hz, 1 H, H-7'), 7.12 (d, $J_{4',6'}$=2.2 Hz, 1 H, H-4'), 7.02 (dd, $J_{6',7'}$=8.8 Hz and $J_{4',6'}$=2.2 Hz, 1 H, H-6'), 4.37 (t, J=7.0 Hz, 2H, $CH_2N$), 4.30 (q, J=7.1 Hz, 2H, $CH_2CH_3$), 4.29 (q, J=7.1 Hz, 2H, $CH_2CH_3$), 3.23 (t, J=4.7 Hz, 4H, piperazinyl methylene), 2.94 (t, J=7.5 Hz, 2H, $CH_2CH_2CH_2N$), 2.78 (t, J=4.7 Hz, 4H, piperazinyl methylene), 2.45 (s, 3, $NCH_3$), 2.36 (quintet, J=7.0 Hz, 2H, $CH_2CH_2CH_2$), 1.32 (t, J=7.1 Hz, 3H, $CH_2CH_3$), 1.29 (t, J=7.1 Hz, 3H, $CH_2CH_3$). $^{13}C$ NMR δ 163.97, 161.17, 157.17, 153.84, 149.38, 141.64, 140.35, 137.62, 136.11, 126.27, 125.52, 122.26, 116.65, 116.45, 102.46, 63.06, 62.44, 56.00 (×2), 51.46 (×2), 47.45, 45.72, 30.08, 26.75, 14.52, 14.33. Anal. ($C_{31}H_{36}N_8O_4 \cdot \frac{1}{2}H_2O$) C,H,N.

To a slurry of $LiAlH_4$ (4 mol eq, 12.3 mmol, 0.47 g) in dry THF (20 mL) at 0° C. under $N_2$ was added dropwise a solution of the diester (XXXIII) (1.80 g, 3.08 mmol) in dry THF (100 mL). After addition was complete the reaction was stirred for 2 h and then water (~5 mL) and 5M NaOH (~5 mL) were alternately added dropwise until the excess $LiAlH_4$ had been quenched. The resulting suspension was filtered through a pad of celite which was washed with hot THF. The celite and lithium salts were then soxhlet extracted with THF/MeOH (99:1) for 5 days, with the solvent being changed every 24 h. The combined filtrate and soxhlet extractions were concentrated at reduced pressure and the residue chromatographed on alumina (grade III) with gradient elution from MeOH/EtOAc (9:1) to MeOH/EtOAc (7:3) to give compound 24 of Table 1 (0.80 g, 52% yield) as a white solid. A small amount was recrystalised from EtOAc/MeOH to provide an analytically pure sample, mp 238–240° C. $^1H$ NMR ($CD_3OD$) δ 8.20 (br s, 1 H, H-4), 7.93 (br d, $J_{6,7}$=8.4 Hz, 1 H, H-6), 7.67 (s, 1H, H-2"), 7.62 (br d, $J_{6,7}$=8.4 Hz, 1 H, H-7), 7.49 (d, $J_{6',7'}$=8.8 Hz, 1 H, H-7'), 7.12 (br s, 1 H, H-4'), 7.02 (dd, $J_{6',7'}$=8.8 Hz and $J_{4',6'}$=2.3 Hz, 1 H, H-6'), 4.66 (s, 2H, $CH_2OH$), 4.52 (s, 2H, $CH_2OH$), 4.18 (t, J=7.1 Hz, 2H, $CH_2N$), 3.21 (br t, J=4.5 Hz, 4H, piperazinyl methylene), 2.96 (t, J=7.4 Hz, 2H, $CH_2CH_2CH_2N$), 2.66 (br t, J=4.5 Hz, 4H, piperazinyl methylene), 2.39 (quintet, J=7.1 Hz, 2H, $CH_2CH_2CH_2$), 2.36 (s, 3, $NCH_3$). $^{13}C$ NMR δ 157.52, 153.79, 149.61, 140.04, 138.41, 129.89, 125.58, 122.26, 116.45, 57.49, 56.16 (×2), 52.79, 51.83 (×2), 46.10, 45.44, 29.96, 26.80. Anal. ($C_{27}H_{32}N_8O_2$) C,H,N.

To a suspension of the diol (compound 24 of Table 1) (102 mg, 0.204 mmol) in dry $CH_2Cl_2$ (10 mL) was added methyl isocyanate (2.5 mol eq, 0.509 mmol, 21 mL) and dibutyl tin diacetate (2 drops). The suspension was stirred for 6 h and then further 50 mL portions of methyl isocyanate were added every 8 h, until the reaction mixture cleared (~250 mL), after which it was immediately put onto an alumina (grade III) column and chromatographed with gradient elution from EtOAc to MeOH/EtOAc (6:94) to give compound 25 of Table 1 (72 mg, 57% yield) as an off white powder, 176–177° C. $^1H$ NMR ($CD_3OD$) δ 8.22 (br s, 1 H, H-4), 7.94 (br d, $J_{6,7}$=8.2 Hz, 1 H, H-6), 7.75 (s, 1H, H-2"), 7.63 (br s, 1 H, H-7), 7.49 (d, $J_{6',7'}$=8.7 Hz, 1 H, H-7'), 7.14 (br s, 1 H, H-4'), 7.04 (dd, $J_{6',7'}$=8.8 Hz and $J_{4',6'}$=2.3 Hz, 1 H, H-6'), 5.22 (s, 2H, $CH_2OCONHCH_3$), 5.03 (s, 2H, $CH_2OCONHCH_3$), 4.19 (t, J=7.2 Hz, 2H, $CH_2N$), 3.23 (br t, J=5.0 Hz, 4H, piperazinyl methylene), 2.97 (t, J=7.6 Hz, 2H, $CH_2CH_2CH_2N$), 2.68 (partially obscured t, J=4.9 Hz, 4H, piperazinyl methylene), 2.66 (s, 3, $CH_3NHCO$), 2.64 (s, 3H, $CH_3NHCO$), 2.38 (s, 3, $NCH_3$), 2.37 (partially obscured quintet, J ~7.3 Hz, 2H, $CH_2CH_2CH_2$). HRMS (FAB, 70 eV) Calculated for $C_{31}H_{39}N_{10}O_4$: 615.3156. Found: 615.3130.

EXAMPLE 19

Interaction of Representative Compounds of the Invention with DNA

The interaction of compounds 2 to 6 with DNA was examined.

Reversible DNA binding constants and binding site sizes for calf thymus DNA at 20° C. in 0.01M HEPES buffer, pH 7.00 were determined spectrophotometrically by Scatchard analysis, using analysis times sufficiently short that covalent alkylation reactions did not interfere. The reversible binding of these compounds is 3 to 4 fold stronger than that of pibenzimol itself, and decreases slightly across the homologous series. The binding site size remains essentially constant at 2.6±0.4 nucleotides per binding site, suggesting similar binding contacts across the series. These results are summarized in Table 2.

TABLE 2

Binding of Representative Compounds of the Invention to DNA

| Compound | Intrinsic Association constant ($10^{-6}$) | Site size (Number of nucleotide residues) |
|---|---|---|
| Pibenzimol | 1.82 | 2.4 |
| 2 | 7.52 | 2.6 |
| 3 | 6.73 | 3.0 |
| 4 | 6.30 | 2.8 |
| 5 | 4.55 | 3.0 |
| 6 | 3.89 | 2.4 |

The mustards (compounds 1 to 6) all bind 3 to 4 fold more tightly to calf thymus DNA at 0.01 ionic strength than does pibenzimol itself. Although the binding constants decrease by a factor of nearly 2 as the linker chain is increased, the binding site size n' remains essentially constant at 2.6±0.4 nucleotides per binding site, suggesting that the mode of binding and the drug/DNA contacts which comprise it are similar, and dictated by the bisbenzimidazole chromophore.

EXAMPLE 20

DNA Crosslinking Assay

The ability of representative compounds of the invention to bind to and cross-link DNA was examined. This was carried out by agarose gel electrophoresis of plasmid DNA using linearized pSV2gpt DNA (Tindall, K. R. and Stankowski, L. F.; Mutation Research, 1989 220 241–245) and the method reported by Valu et al, 1990, op.cit. Briefly, linearized pSV2gpt DNA (1 μL of a 1 mg/mL solution) was incubated with drug in TE-80 buffer (10 mM Tris.HCl, 1 mM EDTA at pH 8), shielded from ambient light, for 2 h at 30° C., then denatured by the addition of 2 gL of 1% sodium dodecyl sulfate and 10 μL of 50 mM methylmercury hydroxide and incubated for a further 30 min at 20° C. in the dark. Renaturation of drug-treated DNA samples was carried out by incubation with 2.5 μL of 2-mercaptoethanol for 1 h. Samples were prepared for electrophoresis by the addition of 0.1 mg/mL bromophenol blue, 0.5 μg/mL ethidium bromide and 5 μL of 40% sucrose. Electrophoresis was carried out at 120V in 89 mM tris/borate buffer at pH 8 containing 2 mM EDTA and 0.5 μg/mL ethidium bromide. DNA was visualized using 302 nm trans-illumination, and was photographed using Polaroid type 55 film and a Wratten 3A filter.

An illustration of the gels is provided in FIG. 1, and a summary of the data is given in Table 3.

TABLE 3

Ability of Representative Compounds of the Invention to Alkylate and/or Cross-Link DNA

| Compound | Rate constant for alkylation ($S^{-1}$) | Cross-linking |
|---|---|---|
| 1 | Not done | No |
| 2 | $1.78 \times 10^4$ | No |
| 3 | $3.01 \times 10^4$ | No |
| 4 | $4.62 \times 10^4$ | No |
| 5 | $6.52 \times 10^4$ | No |
| 6 | $9.64 \times 10^4$ | Yes |

After drug treatment, DNA is denatured to the single stranded form, which runs as a lower band in the gels (see lanes 1 and 2 in FIG. 1). Cross-linking by the drugs is evidenced by the appearance of increasing amounts of renatured, double stranded DNA, as shown by the upper band in the gels, corresponding to the band for untreated DNA seen in lane 1. The conditions used were similar to those employed in the yeast assays (see Example 17 below), and only the compound with the longest alkyl chain (compound 6) crosslinked DNA under these conditions.

As shown in Table 3, the compounds all bind strongly to DNA. The gel electrophoresis studies show that the analogues 2 to 6 do not unwind closed circular supercoiled DNA, suggesting strongly that these compounds bind in the minor groove, as does pibenzimol. The kinetic data indicate different rates of alkylation of DNA. While the slower rates for compounds 2 and 3 are largely explained by the lower reactivities of these mustards, the increase from compound 4 to compound 6 is probably related to their decreasing DNA binding allowing more conformational freedom for the drug, a phenomenon observed previously with DNA-targeted alkylators. However, cross-linking was only detected for the compound of longest chain length, compound 6. It is of considerable interest that this compound was not the most effective antitumour drug, and it appears that cross-linking is not important for antitumour activity in these drugs, as shown previously for other minor groove-targeted monoalkylating agents (Warpehoski, M. H. et al, J. Med. Chem., 1988 31 590–603).

The rate constants for alkylation of calf thymus DNA, determined by measuring the rate of increase in the DNA-bound fluorescence, are also given in Table 3, and show that the compounds alkylate DNA more rapidly as the chain length increases.

EXAMPLE 21

Anti-Tumour Activity In Vitro

Representative examples of compounds of the invention were tested for biological activity against tumors. Compounds 1 to 6 and 14 to 21, prepared as described above, were tested for their ability to inhibit growth in vitro of cells of the wild-type murine leukaemia cell line P388, and the cell line AA8 which is derived from Chinese hamster ovary cells. For each compound, the $IC_{50}$, ie. the concentration of compound which inhibited cell growth in treated cultures to 50% of that of controls, was determined, using means of three determinations. In addition, a hypersensitivity factor was determined by comparing activity of the compounds against AA8 cells to activity against UV4. The latter cell line is deficient in aspects of the excision repair pathway for removing DNA adducts, and is hypersensitive to DNA-alkylating agents, especially interstrand crosslinking agents. Previous work has shown that the ratio of $IC_{50}$s determined in the wild-type AA8 and mutant UV4 lines (the hypersensitivity factor HF) is a determinant of the mode of cell killing by alkylating agents (Palmer, B. D. et al, J. Med. Chem., 1990 33 112–121; Wilson, W. R. et al, J. Med. Chem., 1989 32 31–38). Compounds with HFs of ca. 1 are unlikely to kill cells via DNA alkylation events. Compounds which show high HF values are likely to form bulky adducts or cross-links, with the latter being especially likely for compounds showing the highest HF values (>ca. 25) (Wilson et al, op. cit.).

Cell lines were maintained in exponential growth phase by subculturing in RPMI 1640 (P338) or Alpha MEM (AA8, UV4) containing 10% fetal calf serum, as previously described (Palmer et al, op.cit.; Baguley, B. C. and Wilson, W. R., Eur. J. Cancer Clin. Oncol., 1987 23 607–613). $IC_{50}$ values were determined using log-phase cultures in 96-well microculture plates, and were calculated as the nominal drug concentration required to reduce the cell density to 50% of control values, using 8 control cultures on each microplate. For P388 cultures, drug was present throughout the growth period (72 h), and final cell densities were determined using a minor modification of the MTT method of Mossman (Mossman, T., J. Immunol. Methods, 1983 65 55–63). For AA8 and UV4 cultures, drug exposure was terminated after 18 h by washing three times with fresh medium. Cultures were then grown for a further 72 h before determining cell density by staining with methylene blue (Finlay, G. J. et al, Anal. Biochem., 1984 139 272–277). The results are summarized in Table 4.

TABLE 4

| | Growth Inhibition In Vitro | | |
|---|---|---|---|
| Compound | $IC_{50}$ (μM) | | Hypersensitivity |
| Number | P338 cells | AA8 cells | factor |
| 1 | 0.5 | 5.75 | 14 |
| 2 | 0.8 | 1.68 | 24 |
| 3 | 0.85 | 1.50 | 59 |
| 4 | 0.01 | 0.33 | 47 |
| 5 | 0.02 | 1.32 | 46 |
| 6 | 0.06 | 0.4 | 20 |
| 14 | 0.74 | | |
| 15 | 0.12 | | |
| 16 | 0.37 | | |
| 17 | 0.09 | | |
| 18 | >1.0 | | |
| 19 | <0.06 | | |
| 20 | 0.61 | | |
| 21 | <0.06 | | |

In the present series, both of the non-alkylating compounds (pibenzimol itself and the $N(Et)_2$ derivative) were moderately cytotoxic against wild-type P388 leukaemia, with $IC_{50}$ values of ca. 1 μM. The compounds were much less active against the AA8 cell line (although a shorter exposure time was used as described above). In other studies, pibenzimol has shown a similar $IC_{50}$ value against L1210 leukaemia, but very low cytotoxicity in solid tumour lines (Finlay, G. J. and Baguley, B. C., Eur. J. Cancer, 1990 26 585–589). Both pibenzimol and the $N(Et)_2$ compound had AA8/UV4 $IC_{50}$ ratios (HFs) of about unity, as expected for compounds which do not act by DNA alkylation. Some Phase I–II clinical studies with pibenzimol have been reported, but the mode of action is not known (Patel, S. K. et al, Invest. New Drugs, 1991 9 53–57; Chen, A.Y. et al, Cancer Res., 1993 53 1332–1337).

The half-mustard analogue (1) showed slightly increased cytotoxicity against the wild-type P388 and AA8 lines, but was much more effective against UV4, resulting in an HF of 14. This is strong evidence for the mode of cytotoxicity being via the formation of DNA adducts. The corresponding full mustard (2) had roughly similar cytotoxicities against the wild-type lines, but had an increased HF of 24. This compound has the capability of forming DNA cross-links, and the increased HF is consistent with this possibility. Compounds 3 to 6 form a series where the aniline mustard moiety is tethered to the end of an increasingly long polymethylene chain. While $IC_{50}$ values in both wild-type cell lines differ little between compounds 2 and 3, there is a large increase in cytotoxicity (80-fold in P388, 5-fold in AA8) for the $(CH_2)_2$-linked compound 4. This is probably not due simply to increasing lipophilicity, since the longer chain compounds 5 and 6 are less cytotoxic.

The relative cytotoxicities of compounds 2 to 6 do suggest a positive role for the DNA-targeting chromophore. The increased HF of compounds 3 to 5 is consistent with them forming a higher proportion of crosslinks than compound 2. The lower HF and absolute cytotoxicity of compound 6 suggest that there may be an optimal chain length, beyond which entropic factors become important. We have noted this phenomenon previously in a series of acridine-targeted mustards (Valu, K. K. et al, J. Med. Chem., 1990 33 3014–3019).

EXAMPLE 22

Anti-Tumour Activity In Vivo

In addition, the ability of the compounds to increase the percentage life span of mice bearing P338 murine leukaemia was assessed. The compound was administered intraperitoneally, as a single dose of a solution in point 1 mL of 30% v/v ethanol/water, 24 hrs after intraperitoneal inoculation of $10^6$ tumour cells. There were six animals in each group. The percentage increase life span of treated animals was determined by comparing with control animals which had been injected with an equivalent volume of normal saline. An increase in life-span of more than 20% is considered to be statistically significant. The results are summarized in Table 5.

TABLE 5

Effect of Compounds In Vivo

| Compound Number | Optimal dose (mg/kg) | % Increase in lifespan |
|---|---|---|
| 1 | 30 | 86 |
| 2 | 30 | 106 (2) |
| 3 | 13.3 | 71 |
| 4 | 3.9 | 52 (1) |

TABLE 5-continued

Effect of Compounds In Vivo

| Compound Number | Optimal dose (mg/kg) | % Increase in lifespan |
|---|---|---|
| 5 | 5.9 | not active |
| 6 | 8.9 | 23 |

Figures in parenthesis represent the average number of animals in a group of six which were long-term survivors. Compound 5 was inactive in vivo at all doses up to the maximum tolerable dose.

Pibenzimol is reported to have moderate in vivo activity against L1210 leukemia on a repeated dose schedule (Chen et al, op.cit.), but was not active against P388 using the single-dose protocol. However, the $N(Et)_2$ derivative showed low but significant activity (ILS 50%). The monoalkylating half-mustard (1) was also active, but the highest activity was shown by the corresponding bis-mustard(2), with a single dose of 30 milligrams/kilogram resulting in some long-term survivors. The antitumour activity of the higher homologues decreased as their toxicity increased, but the $CH_2$ and $(CH_2)_2$ compounds 3 and 4 retained significant in vivo activity.

It is clear from the data in Examples 21 and 22 that compounds 1 to 6 and 14 to 21, representative examples of the compounds of general formula I, are potent cytotoxic agents in vitro, and that compounds 1 to 4 also possess in vivo anticancer activity. While compound 5 was inactive in the particular assay described in Example 22, it is understood in the art that there can be considerable differences in response between different types of in vivo assay. Other assays are known, for example using different tumour cell lines or using primary tumors.

The present study has shown that mustard analogues of the well-characterised reversible minor groove binding ligand pibenzimol have greatly increased cytotoxicity and in vivo antitumor activity in antiproliferative assays, compared with pibenzimol itself.

EXAMPLE 23

Bacterial Mutagenicity

The ability of representative compounds of the invention to induce mutations in bacteria was assayed using a standard plating method. Salmonella strains TA1977, TA1978, TA98 and TA100 were kindly supplied by B. N. Ames (Biochemistry Dept, University of California, Berkeley, Calif., USA). All are deep rough derivatives of the LT2 subline of S. typhimurium. Characteristics of these strains and the rationale for their selection have been previously described (Ferguson, L. R. et al, Mutation Research, 1988 265 103–104). Since we have found that the use of aliquots of frozen stock is necessary for reproducibility of experiments, the bacteria were initially grown to stationary phase in nutrient media and frozen (with 10% DMSO) in 1 ml aliquots at −80° C. Strains were routinely characterised for spontaneous reversion characteristics and reversion rates in response to the following diagnostic mutagens: TA 98; daunomycin (Sigma) and 4-nitro-o-phenylene diamine (Sigma): TA100; sodium azide (BDH): TA102; bleomycin: TA1978pKM101; mitomycin C: TA1537; 9-aminoacridine (Sigma).

For each experiment, a 1 mL vial of bacteria was removed from the −80° C. freezer, inoculated into 20 mL of fresh bacterial complete medium and grown for 4 hours. Optical density was checked at that time and at intervals thereafter until a one-in-ten dilution into fresh bacterial complete medium gave a reading of between 0.10 and 0.12 at 654 nm, to ensure that all cultures were at the same stage of growth when used. The *S. typhimurium* plate incorporation assay was carried out as described (Maron, D. M. and Ames, B. N., Mutation Research, 1983 113 173–215). Each drug was tested over a range of concentrations by adding varying amounts to 2 mL of soft agar containing 5 mM histidine-biotin maintained at 42° C. in a temperature block. Bacterial suspension (100 µL) was added, the tube was mixed and quickly poured over the surface of agar plates containing 20 mL of minimal medium (Vogel, H. J. and Bonner, D. M., J. Biol. Chem., 1956 218 97–106). Plates were allowed to harden and then incubated at 37° C. for 3 days before scoring colonies for reversion to histidine independence. All assays were performed in triplicate, and repeated at least once. Data presented are an average. Reversion characteristics of each strain were routinely tested in each experiment. Care was taken to exclude light from both the chemical and the assay plates. Colony counts were determined on an Artek Model 880 automatic counter, calibrated with plates counted manually (Maron and Ames, op.cit.).

The compounds were tested in a number of strains, and were found to be completely negative in TA98, TA1978pKM101 and TA1537. Some compounds showed activity in strains TA100 and TA102, and dose-response curves for these are summarised in Table 6.

TABLE 6

Bacterial Mutagenicity Data for Compounds of the Invention

| Compound | Concentration (µg/plate) | TA98 | TA100 | TA102 |
|---|---|---|---|---|
| Pibenzimol | 0 | 60 ± 9 | 187 ± 4 | 246 ± 6 |
| | 4 | 59 ± 3 | 188 ± 11 | 275 ± 12 |
| | 10 | 64 ± 8 | 191 ± 7 | 277 ± 1 |
| | 20 | 55 ± 6 | 179 ± 6 | 301 ± 3 |
| | 40 | 61 ± 5 | 168 ± 13 | 377 ± 49 |
| | 80 | 62 ± 9 | 178 ± 11 | 397 ± 10 |
| 1 | 0 | 60 ± 9 | 187 ± 4 | 296 ± 41 |
| | 4 | 70 ± 3 | 196 ± 23 | 406 ± 20 |
| | 10 | 62 ± 7 | 162 ± 21 | 417 ± 26 |
| | 20 | 67 ± 9 | 172 ± 13 | 442 ± 62 |
| | 40 | 52 ± 7 | 226 ± 23 | 442 ± 43 |
| | 80 | 65 ± 3 | 207 ± 12 | [194 ± 60] |
| | 120 | [53 ± 39] | [155 ± 39] | [82 ± 48] |
| 2 | 0 | 60 ± 9 | 187 ± 4 | 296 ± 41 |
| | 4 | 61 ± 3 | 173 ± 7 | 408 ± 31 |
| | 10 | 68 ± 2 | 175 ± 17 | 371 ± 14 |
| | 20 | 58 ± 1 | 167 ± 28 | 280 ± 14 |
| | 40 | 52 ± 7 | 210 ± 20 | [274 ± 12] |
| | 80 | 55 ± 2 | 192 ± 1 | [51 ± 7] |
| | 120 | [48 ± 2] | [185 ± 14] | [10 ± 1] |
| 3 | 0 | 72 ± 5 | 150 ± 17 | 296 ± 41 |
| | 4 | 71 ± 2 | 154 ± 8 | 297 ± 38 |
| | 10 | 83 ± 1 | 130 ± 10 | 237 ± 64 |
| | 20 | 87 ± 6 | 137 ± 43 | 304 ± 16 |
| | 40 | 86 ± 5 | 167 ± 24 | 268 ± 59 |
| | 80 | 77 ± 10 | 167 ± 8 | [377 ± 35] |
| | 120 | 86 ± 8 | 157 ± 12 | 505 ± 121 |
| 4 | 0 | 72 ± 5 | 150 ± 17 | 296 ± 41 |
| | 4 | 71 ± 2 | 172 ± 4 | 340 ± 26 |
| | 10 | 74 ± 10 | 231 ± 7 | 366 ± 49 |
| | 20 | 75 ± 1 | 264 ± 12 | 429 ± 17 |
| | 40 | 65 ± 6 | 237 ± 29 | 465 ± 41 |
| | 80 | [61 ± 9] | 207 ± 10 | 609 ± 74 |
| | 120 | [55 ± 6] | 232 ± 19 | [564 ± 19] |
| 5 | 0 | 60 ± 9 | 187 ± 4 | 296 ± 41 |
| | 4 | 63 ± 2 | 188 ± 15 | 342 ± 32 |

TABLE 6-continued

Bacterial Mutagenicity Data for Compounds of the Invention

| Compound | Concentration (µg/plate) | TA98 | TA100 | TA102 |
|---|---|---|---|---|
| | 10 | 62 ± 1 | 180 ± 5 | 392 ± 31 |
| | 20 | 71 ± 13 | 205 ± 14 | 368 ± 32 |
| | 40 | 62 ± 3 | 240 ± 7 | 327 ± 17 |
| | 80 | 63 ± 9 | 258 ± 21 | 480 ± 17 |
| | 120 | 71 ± 1 | [204 ± 28] | 607 ± 28 |
| 6 | 0 | 72 ± 5 | 150 ± 17 | 296 ± 41 |
| | 4 | 65 ± 10 | 160 ± 13 | 271 ± 31 |
| | 10 | 69 ± 7 | 136 ± 0 | 386 ± 10 |
| | 20 | 68 ± 8 | 156 ± 29 | 342 ± 14 |
| | 40 | 69 ± 9 | 144 ± 10 | 372 ± 19 |
| | 80 | 96 ± 5 | 142 ± 10 | 336 ± 19 |
| | 120 | 75 ± 3 | 157 ± 14 | 353 ± 34 |

Results are mean values (2 experiments, plated in triplicate)±standard deviation.

Square brackets denote that toxicity was becoming apparent on visual inspection of the plates.

The parent compound and the less reactive mustard derivatives 1–3 showed no statistically significant mutagenic response in TA100 when the data were analysed by a standard method (Mahon, G. A. T. et al, 1989, D. J. Kirkland (Ed.), Statistical evaluation of mutagenicity test data. Cambridge University, Cambridge). However, if the more toxic dose levels were not included in the analysis, compounds 4 and 5 could be considered to show a mutagenic effect in TA100. In TA102, the parent compound showed a weak but significant mutagenic effect. The more reactive mustard analogues 3–5 were also active in TA102, the last two more so than the parent compound.

None of the compounds showed any evidence of frameshift mutagenesis in GCGC regions, as shown by inactivity in the strains TA98 and TA1978pKM101. They were also inactive against TA1978+, which was included as an example of a uvrB+ strain, a genotype which we have previously found necessary to detect frameshift mutagenesis by cross-linking drugs such as mitomycin C (Ferguson, L. R. et al, Antitumour Drug Design, 1988 3 67–76). The compounds were also non-mutagenic in strain TA1537 (McCoy, E. C. et al, Mutation Res., 1981 90 21–30; Ferguson L. R. and von Borstel, R. C., Mutation Res., 1992 265 103–148), and thus appeared to be quite different to the series of acridine-targeted aniline mustards studied earlier (Ferguson, L. R. et al, Anticancer Drug Design, 1989b 4 209–216 and Ferguson, L. R. and Turner, P. M., Eur. J. Cancer Clin. Oncol., 1989c 24 591–596) and also to the parent aniline mustards (Ferguson, L. R. et al, Mutation Res., 1989a 224 95–104). The mutagenic ability of compounds 4 and 5 in TA100 is consistent with DNA monoalkylation by these compounds, as is their activity in causing weak mitotic crossing-over and some aberrant colonies in yeast. The lower bacterial mutagenicity and increased mitotic crossing-over activity of compound 6 are consistent with its DNA cross-linking capability.

Both the parent compound and several mustard analogues did show activity in strain TA102. This strain carries the hisG428 ochre (TAA) mutation (Levin et al, 1982), and detects as mutagens a variety of oxidants and other compounds not detected by the other tester strains. The hisG428 mutation has A:T base pairs at the mutated site, while the other standard tester strains have G:C base pairs at the critical site. Both the parent compound (non-alkylating) and the mustard analogues of the mutation show similar effects, which may be due more to their high binding selectivity for AT sequences than to any alkylation event. Overall, these results support the view that the pibenzimol chromophore may be redirecting mustard alkylation to unusual sites, presumably in the minor groove, as has been shown for other targeted mustards (Prakash, A. S. et al, Anti-Cancer Drug Design, 1991 6 195–206).

EXAMPLE 24

Mitotic Crossing-Over and Petite Mutagenesis in Yeast

Many anti-cancer agents are themselves mutagenic, and therefore may give rise to other cancers as a side-effect of treatment. This may result from mutagenesis of mitochondrial DNA. The effect of representative compounds of the invention on mitochondrical mutagenesis in yeast was therefore examined.

The *Saccharomyces cerevisiae* diploid strain D5 (Zimmermann, F. K., Mutation Res., 1973 21 263–269) was kindly provided by Dr B. S. Cox (Botany School, University of Oxford). A single colony isolate was inoculated into liquid yeast complete medium (YC; Cox, B. S. and Bevan, E. A., New Phytol, 1962 61 342–351) and grown to stationary phase for 24 h. Dimethyl sulphoxide was added to 10%. Aliquots (1 mL) were frozen to −70° C., and stored at this temperature before use. For all experiments, the 1 mL sample was thawed, added to 10 mL of fresh medium and grown for exactly 2 hours before use.

This assay has been described in detail (Ferguson, L. R., Mutation Res., 1984 136 223–234). Briefly, a log-phase culture was washed, then diluted into 0.87% saline. A 96-well microtitre tray (A/S Nunc, Denmark) was inoculated with (usually) 100 µL aliquots of the diluted yeast culture, and compounds added at various dilutions to the wells, to a maximum of 1000 µg/mL. Compounds were dissolved in dimethyl sulphoxide, and dilutions made so that there was no more than 1% DMSO in each well. Trays were incubated for either 2 hours or 20 hours at 30° C., an appropriate dilution made from each well into saline, and 100 µL plated onto each of 10 YC plates. Cell numbers were calculated so that the dilutions at this point were at least 1/10$^4$, thereby effectively washing compounds from cells by dilution (Ferguson, 1984, op.cit.). Plates were incubated at 30° C. for 5 days, and scored for ordinary, coloured or sectored colonies by visual inspection (Zimmermann, 1973, op.cit.). They were then overlayed with tetrazolium in order to score petite colonies (Nagai, S., Science, 1959 130 1188–1189). All experiments were performed at least twice, and the data compared for reproducibility. The data presented have been pooled.

Dose response data for each of the compounds are summarised in Table 7. Compounds 1 to 3 caused no significant activity in either of these assays. However, the more reactive mustard compounds 4 to 6 caused mitotic crossing-over, with the effect increasing with chain length; compound 6 is a moderately effective inducer of mitotic crossing-over. This was the only compound which also showed activity, albeit weak in the petite mutagenesis assays.

TABLE 7

Petite Mutagenesis, Mitotic Crossing Over and Total Aberrant Colonies Following 2h Incubation of Drugs With Saccharomyces Strain D$_5$ Under Non-Growing Conditions

| Compounds | Concentration (mg/ml) | Survival[a] | Petites[b] | MR[c] | TA[d] |
|---|---|---|---|---|---|
| Pibenzimol | 0 | 100(4965) | 0.4 | 0.04 | 0.28 |
|  | 0.15 | 90.5(4499) | 0.5 | 0.04 | 0.22 |
|  | 0.313 | 71.9(3560) | 0.4 | 0.05 | 0.22 |
|  | 0.625 | 40.9(2033) | 0.7 | <.05 | 0.18 |
|  | 1.25 | 24.6(1220) | 1.8 | <.08 | 0.33 |
| 1 | 0 | 100(5100) | 0.4 | .04 | 0.31 |
|  | 1.25 | 98.1(4997) | 0.5 | <.04 | 0.25 |
|  | 2.5 | 87.8(4478) | 0.4 | .05 | 0.25 |
|  | 5 | 69.8(3562) | 0.3 | .06 | 0.29 |
|  | 10 | 12.5(638) | 0.3 | <.1 | 0.31 |
| 2 | 0 | 100(5620) | 0.5 | <.02 | .19 |
|  | .04 | 88.6(5566) | 0.4 | .04 | .23 |
|  | .08 | 70.9(4457) | 0.4 | .02 | .22 |
|  | .15 | 65.4(4106) | 0.6 | .05 | .45 |
|  | .33 | 33.6(2101) | 0.6 | <.05 | .20 |
| 3 | 0 | 100(6081) | 0.5 | <.02 | .26 |
|  | .08 | 83.5(5246) | 0.4 | <.02 | .23 |
|  | .15 | 75.0(4714) | 0.4 | <.02 | .25 |
|  | .31 | 48.3(3034) | 0.5 | .06 | .20 |
|  | .63 | 14.3(896) | 1.8 | <0.1 | .23 |
| 4 | 0 | 100(5374) | 0.5 | .04 | .26 |
|  | 1.25 | 82.3(4421) | 0.4 | <.04 | 0.18 |
|  | 2.5 | 81.9(4402) | 0.6 | <.04 | 0.36 |
|  | 5 | 66.2(3558) | 0.4 | .06 | 0.45 |
|  | 10 | 36.6(1892) | 0.4 | .21 | 0.62 |
| 5 | 0 | 100(4672) | 0.5 | .04 | .26 |
|  | 1.25 | 85.8(4009) | 0.7 | .05 | .26 |
|  | 2.5 | 76.3(3565) | 0.7 | .06 | .45 |
|  | 5 | 45.6(2130) | 0.4 | .09 | .47 |
|  | 10 | 17.7(827) | 0.5 | .11 | .94 |
| 6 | 0 | 100(4672) | 0.5 | .04 | .26 |
|  | .04 | 76.2(3566) | 0.6 | 0.11 | .33 |
|  | .08 | 64.3(3008) | 0.8 | 0.26 | .75 |
|  | .15 | 61.3(2863) | 1.1 | 0.28 | .85 |
|  | .3 | 24.7(1151) | 4.5 | 0.36 | .93 |

[a]Survival is expressed as a percentage. The actual numbers of colonies examined are given in brackets
[b]The indication of petite colonies at the given dose, expressed as a percentage of total surviving cells.
[c]Mitotic crossing over, calculated as the frequency of red/pink or red/pink/white colonies as a percentage of total surviving cells.
[d]The total frequency of aberrant colonies, calculated as the number of coloured colonies as a percentage of toal surviving cells.

Previous studies have shown that many minor groove binding drugs are very effective "petite" or mitochondrial mutagens in yeast (Ferguson and Baguley, 1983), an activity which is also seen for both simple nitrogen mustards and those targeted to DNA by an intercalating (acridine) carrier (Ferguson 1988, op.cit.; 1989, op.cit.; 1991, op.cit.). It is therefore of considerable interest that both the parent compound and most of the analogues are not active in this system. Although our results do not rule out some mitochondrial effects for these compounds—for example, some types of mitochondrial enzyme inhibition will not be detected in the petite mutagenesis assay—none of the pr esent series appears to act similarly to the bisquaternary ammonium heterocycle class of minor groove binders (Ferguson and Baguley, 1983, op. cit.). Thus the most effective antitumour agent, the monoalkylator compound 2, was inactive as a bacterial mutagen and as a nitochondrial mutagen in yeast.

The weak mutagenic activity of the bisbenzimidazole-derived mustards of the invention suggests that, unlike many alkylating agents, they may be less likely to be potential carcinogens (Quinto, I. and Radman, M., Mutation Res., 1987 181 235–242; Schmal, D., IRAC Sci. Publ., 1986 78 143–146; Pederson-Bjergaard, J. et al, Cancer Res., 1989 48 1812–1817).

It will be apparent to the person skilled in the art that while the invention has been described in some detail for the purposes of clarity and understanding, various modifications and alterations to the embodiments and methods described herein may be made without departing from the scope of the inventive concept disclosed in this specification.

We claim:
1. A compound of general formula I

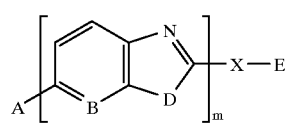

(I)

wherein A represents CN, NHR or any one of the formulae IIa–IId;

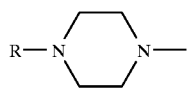

IIa

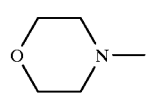

IIb

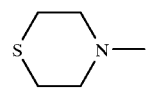

IIc

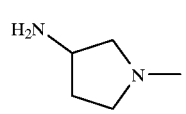

IId

B represents CH;
D represents NH or NR;
X represents $(CH_2)_n$, $(CH_2)_nO$, $(CH_2)_nS$, NHCO, NHCO$(CH_2)_n$, CONH, or CONH$(CH_2)_n$;
E represents any one of the formulae IIIa–IIIC;

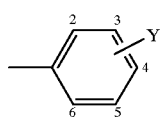

IIIa

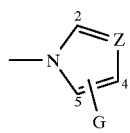

IIIb

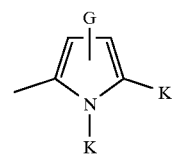

IIIc m is 1 or 2,
n is from 0 to 6, and
R is a lower alkyl group optionally substituted with amine and/or hydroxyl functions;
N-oxides thereof or pharmaceutically acceptable additions salts thereof, with the proviso that in formula IIIa, Y is one of N(HC$_2$CH$_2$O)$_2$, N(Me)CH$_2$CH$_2$O or N(Et)CH$_2$CH$_2$O,
wherein A represents CN, NHR or any one of the formulae IIa–IId; B represents CH; D represents NH, NR; X represents $(CH_2)_n$, $(CH_2)_nO$, $(CH_2)_nS$, NHCO, NHCO$(CH_2)_n$, CONH, CONH$(CH_2)_n$; E represents any one of the formulae IIIa–IIIc; m is 1 or 2, n is from 0 to 6, and R is a lower alkyl group optionally substituted with amine and/or hydroxyl functions,

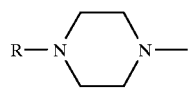

IIa

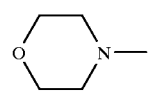

IIb

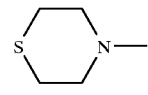

IIc

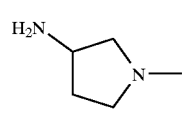

IId

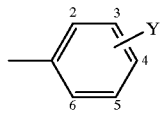

IIIa

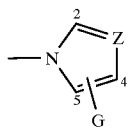

IIIb

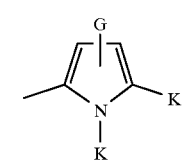

IIIc together with N-oxides or pharmaceutically acceptable addition salts thereof, with the proviso that when A is IIa (where R=Me), B is CH, D is NH; X is a direct link and E is IIIa, then Y in IIIa is not 4—$N(CH_2CH_2Cl)_2$, In formula IIa, R is a lower alkyl group is optionally substituted with amine and/or hydroxyl functions, In formula IIIa, Y is up to two of $N(CH_2CH_2Q)_2$, $N(Me)CH_2CH_2Q$, $N(Et)CH_2CH_2Q$, $NO_2$, Cl, Br, F, OMe, Me or $CONH_2$ at positions 2 to 6, and Q is Cl, Br, I, OH or $OSO_2Me$, In formula IIIb, G is up to two of COOR, $CH_2OCHONHR$, $CH_2Q$, where R is a lower alkyl group optionally substituted with amine and/or hydroxyl functions, and Q is Cl, Br, I, OH or $OSO_2Me$, and Z is =N— or —CH=, In formula IIIc, G is up to two of COOR, $CH_2OCONHR$, or $CH_2Q$, where R is a lower alkyl group optionally substituted with amine and/or hydroxyl together with up to one of $NO_2$, Cl, Br, F, OMe, Me or $CONH_2$ at positions 2 to 6, and Q is Cl, Br, I, OH or $OSO_2Me$, and further with the proviso that when A is IIa (where R=Me), B is CH, D is NH, X is $(CH_2)_n$, n is 0, m is 1 and E is IIIa, then Y in IIIa is not 4-$N(CH_2CH_2Cl)_2$, 2-OMe, 3-OMe, 4-OMe, 3-Me, 4-Me, 2-Cl, 3-Cl, 4-Cl, 2-$NO_2$, 3-$NO_2$, 4-$NO_2$, 4-$NO_2$ or 4-$NMe_2$, and in formula IIIb and IIIc G is up to two of COOR, $CH_2OCONHR$ or $CH_2Q$, where R is a lower alkyl group optionally substituted with amine and/or hydroxyl functions, Q is Cl, Br, I, OH or $OSO_2$, Me, Z in formula IIIb is =N— or —CH= and the K groups in formula IIIc are separately H, Me, or together form a carbocyclic ring —$(CH_2)_3$—.

2. A compound according to claim 1, wherein A represents CN, NHR, or any one of the formulae (IIa–IId).

3. A compound according to claim 2, wherein A is CN or formula IIa.

4. A compound according to claim 1, wherein X represents $(CH_2)_n$ and n is from 0 to 6.

5. A compound according to claim 1, wherein E is formula IIIa or IIIb.

6. A compound according to claim 1, wherein G in formula IIIc is up to 2 of $CH_2OCONHR$ or $CH_2Q$.

7. A compound according to claim 1 selected from the group consisting of 2-[2-[4-(N-methyl-N-(2-chloroethyl)amino)phenyl]-5-benzimidazolyl]-5-(1-methyl-4-piperazinyl)benzimidazole, 2-[2-[4-(N, N-bis(2-chloroethyl)amino)phenyl]-5-benzimidazolyl]-5-(1-methyl-4-piperazinyl)benzimidazole, 2-[2-[[4-(N,N-bis(2-chloroethyl)amino)phenyl]methyl]-5-benzimidazolyl]-5-(1-methyl-4-piperazinyl)benzimidazole, 2-[2-[2-[4- (N,N-bis(2-chloroethyl)amino)phenyl]methyl7]-5-benzimidazolyl]-5-(1-methyl-4-piperazinyl)benzimidazole, 2-[2-[3-[4-(N,N-bis(2-chloroethyl)amino)phenyl]propyl]-5-benzimidazolyl]-5-(1-methyl-4-piperazinyl)benzimidazole, 2-[2-[6-[4- (N,N-bis(2-chloroethyl)amino)phenyl]hexyl]-5-benzimidazolyl]-5-(1-methyl-4-piperazinyl)benzimidazole, 2-[4- (N,N-bis(2-chloroethyl)amino)phenyl]-5-cyanobenzimidazole, 2-[2-[4(N,N-bis(2-chloroethyl)amino))phenyl]ethyl)-5-cyanobenzimidazole, 2-[3-[4-(N,N-bis(2-chloroethyl)amino)phenyl]propyl)-5-cyanobenzimidazole, 2[6-[4-(N,N-bis(2-chloroethyl)amino))phenyl]hexyl)-5-cyanobenzimidazole, 2-[3-[4-(N-ethyl]-N-(2-chloroethyl)amino))phenyl]propyl)-5-cyanobenzimidazole, 2-[2-[4-(N-ethyl-N-(2-chloroethyl)amino))pehnyl]ethyl)-5-cyanobenzimidazole, 2-[6-[4-(N-ethyl-N-(2-chloroethyl)amino))phenyl]hexyl)-5-cyanobenzimidazole, 2-[2-[3-[4-(N-ethyl-N-(2-chloroethyl)amino)phenyl]propyl]-5-(1-methyl-4-piperazinyl)benzimidazole, 2-[2-[2-[4-(N-Ethyl-N-(2-chloroethyl)amino)phenyl]ethyl]-5-benzimidazoyl]-5-(1-methyl-4-piperazinyl)benzimidazole, 2-[2-[6-[4-(N-ethyl-N-(2-chloroethyl)amino)phenyl]hexyl]-5-benzimidazolyl]-5-(1-methyl-4-piperazinyl)benzimidazole, 2-[2-[[4-(N-ethyl-N-(2-chloroethyl)amino)phenyl]methyl]-5-benzimidazoyl]-5-(1-methyl-4-piperazinyl)benzimidazole, 2[2-[3-[3-(N,N-bis(2-chloroethyl)amino)phenyl]propyl]-5-benzimidazolyl]-5-(1-methyl-4-piperazinyl)benzimidazole, 2-[2-[3-[3-(N-ethyl-N-(2-chloroethyl)amino)phenyl]propyl]-5-benzimidazolyl]-5-(1-methyl-4-piperazinyl)benzimidazole, 2-[2-[3-[2-(N,N-bis(2-chloroethyl)aminophenyl]propyl]-5-benzimidazolyl]-5-(1-methyl-4-piperazinyl)benzimidazole, 2-[2-[3-[2-(N-ethyl-N-(2-chloroethyl)amino)phenyl]propyl]-5-benzimidazolyl]-5-(1-methyl-4-piperazinyl)benzimidazole, 2-[3-[N-(4,5-bishydroxymethyl)imidazolyl]propyl]-5-(1-methyl-4-piperazinyl)benzimidzole, 2-[3-[N(4,5-bis (methylcarbamoyl)methyl)imidazoly]propyl]-5-(1-methyl-4-piperazinyl)benzimidazole, 2-[2-[3-[N-(4,5-bishydroxymethyl)imidazolyl]propyl]-5-(benzimidazolyl)-5-(1-methyl-4-piperazinyl)benzimidazole, 2-[2-[3-[N-(4,5-bis(methylcarbamoyl)methyl)imidazolyl]propyl]-5-(benzimidazolyl)-5-(1-methyl-4-piperazinyl) benzimidazole.

8. An anti-tumour agent comprising as active ingredient a compound according to claim 1.

9. A pharmaceutical composition comprising a compound according to claim 1, with a pharmaceutically acceptable carrier.

10. A method of synthesis of compound of general formula I according to claim 1, comprising steps selected for the group consisting of a) converting a nitrile to a corresponding imine ether hydrochloride, and reacting said imine ether hydrochloride with a freshly prepared phenylene diamine;

b) treating an acid with borane-dimethyl sulphide to yield an alcohol; converting the alcohol to an aldehyde by oxidation under Swern conditions; reacting the aldehyde with a phenylenediamine to give a monobenzimidazole compound of formula I; converting the monobenzimidazole compound to a corresponding imine ether and coupling with a diaminobenzene derivative by cupric ion-promoted oxidation to yield a bisbenzimidazole compound of formula I;

c) converting a monomustard acid to an aldehyde, coupling the aldehyde with a phenylenediamine to yield a monobenzimidazole compound of formula I together with the corresponding alcohol; converting the monobenzimidazole to the corresponding imine ether, coupling the imine ether with a diaminobenzene derivative and optionally halogenating to yield a monomustard bisbenzimidazole compound of formula I;

d) coupling a carboxylic acid derivative of an aniline mustard or aniline half-mustard with a freshly-prepared benzimidazole phenylenediamine using PPE, to yield a mustard or half-mustard bisbenzimidazole of formula I;

e) converting an imidazole dicarboxylic acid to the corresponding diethyl ester, subjecting said ester to N-alkylation with an alkyl bromide to yield a t-butyl ester derivative, selectively hydrolysing the t-butyl ester derivative to yield a carboxylic acid, converting the carboxylic acid to the acid chloride, coupling said acid chloride to a nitroaniline to yield an amide, subjecting said amide to reduction and acid-catalysed ring closure to yield a benzimidazole, coverting said benzimidazole to the corresponding diol by hydride reduction, and bis-carbamate protecting said diol; and f) directly coupling a carboxylic acid and a freshly prepared phenylenediamine using PPE to yield a bisbenzimidazole, subjecting said benzimidazole to hydride reduction to yield a diol and biscarbamate protecting said diol.

* * * * *